US012781180B2

(12) United States Patent
Mogna et al.

(10) Patent No.: US 12,781,180 B2
(45) Date of Patent: Nov. 3, 2026

(54) GRANULAR BACTERIA GASTROPROTECTED WITH A COATING MATRIX IN CRYSTALLINE FORM, PROCESS FOR THE PREPARATION THEREOF AND COMPOSITIONS THEREOF

(71) Applicant: PROBIOTICAL S.P.A., Novara (IT)

(72) Inventors: Vera Mogna, Novara (IT); Marco Pane, Novara (IT); Serena Allesina, Novara (IT)

(73) Assignee: PROBIOTICAL S.P.A., Novara (IT)

( * ) Notice: Subject to any disclaimer, the term of this patent is extended or adjusted under 35 U.S.C. 154(b) by 846 days.

(21) Appl. No.: 17/775,798

(22) PCT Filed: Nov. 11, 2020

(86) PCT No.: PCT/IB2020/060626
§ 371 (c)(1),
(2) Date: May 10, 2022

(87) PCT Pub. No.: WO2021/094952
PCT Pub. Date: May 20, 2021

(65) Prior Publication Data

US 2022/0389370 A1 Dec. 8, 2022

(30) Foreign Application Priority Data

Nov. 11, 2019 (IT) ........................ 102019000020805

(51) Int. Cl.
*C12N 1/04* (2006.01)
*C12N 1/00* (2006.01)
(Continued)

(52) U.S. Cl.
CPC ............... *C12N 1/04* (2013.01); *C12N 1/005* (2013.01); *C12N 1/20* (2013.01); *C12N 11/04* (2013.01)

(58) Field of Classification Search
CPC . C12N 1/04; C12N 1/005; C12N 1/20; C12N 11/04; A23L 29/065; A61K 8/99; A61K 35/74
See application file for complete search history.

(56) References Cited

U.S. PATENT DOCUMENTS

2007/0098847 A1 5/2007 Teissier
2014/0370107 A1 12/2014 Mogna et al.
2022/0195378 A1 6/2022 Mogna et al.

FOREIGN PATENT DOCUMENTS

CN 108779433 A 11/2018
CN 109480038 A 3/2019
(Continued)

OTHER PUBLICATIONS

Singh et al., Rapid Quantification of the Total Viable Bacterial Population on Human Hands Using Flow Cytometry with SYBR® Green I. Cytometry Part B Sep. 2019; 96B: 397-403 (Year: 2019).*
(Continued)

*Primary Examiner* — Robert B Mondesi
*Assistant Examiner* — Naghmeh Nina Moazzami
(74) *Attorney, Agent, or Firm* — Steinfl + Bruno LLP

(57) ABSTRACT

Crystalline gastroprotected granular bacteria, such as bacterial strains in granular form coated with a lipid coating matrix, preferably in a reduced amount, said lipid coating matrix having a crystalline form and related compositions and process of preparation are described.

33 Claims, 9 Drawing Sheets

Figure 1:
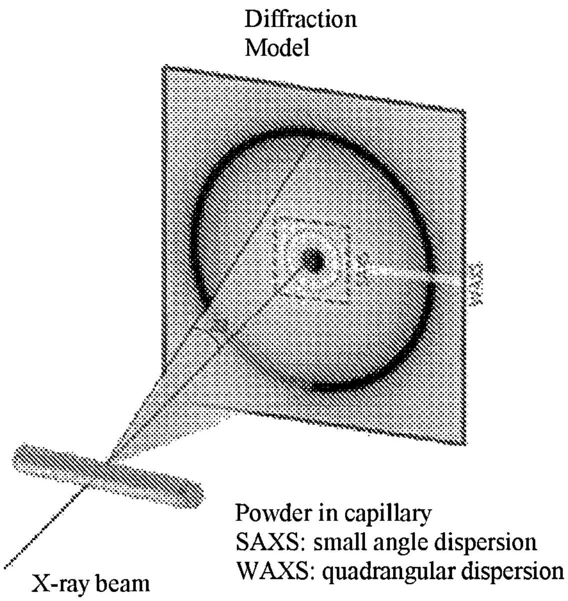

(51) Int. Cl.
*C12N 1/20* (2026.01)
*C12N 11/04* (2006.01)

(56) References Cited

FOREIGN PATENT DOCUMENTS

| | | | | |
|---|---|---|---|---|
| EP | 0383406 | A1 | | 8/1990 |
| IT | 201900006056 | A1 | | 10/2020 |
| JP | H05186336 | A | | 7/1993 |
| JP | H0787950 | A | | 4/1995 |
| JP | 3052131 | U | | 9/1998 |
| JP | H10287574 | A | | 10/1998 |
| JP | 2005519600 | A | | 7/2005 |
| JP | 2007515182 | A | | 6/2007 |
| JP | 2026004349 | A | | 1/2026 |
| KR | 20090071020 | A | | 7/2009 |
| WO | 03/075676 | A1 | | 9/2003 |
| WO | 2010/103374 | A2 | | 9/2010 |
| WO | 2011/110926 | A1 | | 9/2011 |
| WO | WO-2019144979 | A1 | * | 8/2019 |
| WO | 2021/094952 | A1 | | 5/2021 |

OTHER PUBLICATIONS

Marino et al., Potential application of monoglyceride structured emulsions as delivery systems of probiotic bacteria in reduced saturated fat ice cream, LWT-Food Science and Tech, vol. 96, Oct. 2018, p. 329-334 (Year: 2018).*

International Preliminary Report on Patentability for International Application No. PCT/IB2020/060626 filed on Nov. 11, 2020 on behalf of Probiotical S.P.A. Mail Date: May 17, 2022. 6 pages.

International Search Report and Written Opinion for International Application No. PCT/IB2020/060626 filed on Nov. 11, 2020 on behalf of Probiotical S.P.A. Mail Date: Mar. 1, 2021. 9 pages.

Marino M. et al., "Viability of probiotic lactobacillus rhamnosus in structured emulsions containing saturated monoglycerides" *Journal of Functional Foods*, 35, (2017), pp. 51-59.

Akinshina et al. "Effect on monoglycerides and fatty acids on a ceramide bilaryer" Physical Chemistry Chemical Physics 18 (2016): 17446-17460.

Alberts, B. et al. The Lipid Bilayer. Molecular Biology of the Cell. 4th edition. New York: Garland Science (2002). 9 pages.

Communication Pursuant to Article 94(3) EPC and Annex for European Patent Application 20820532.8 filed on Nov. 11, 2020 on behalf of Probiotical S.P.A. Mailed on Sep. 10, 2024. 7 pages.

Fonseca, Fernanda et al., "Factors influencing the membrane fluidity and the impact on production of lactic acid bacteria starters", Applied Microbiology and Biotechnology, (Jul. 12, 2019), vol. 103, pp. 6867-6883. Website: doi.org/10.1007/s00253-019-10002-1.

Kaiser, Hermann-Josef, et al. Order of lipid phases in model and plasma membranes. PNAS, (Sep. 29, 2009), vol. 106, No. 39, pp. 16645-16650.

Office Action for Japanese Patent Application No. 2022-526820 filed on Nov. 11, 2020 on behalf of Probiotical S.P.A. Mailed on Sep. 10, 2024. Original and English summary translation. 8 pages.

Rinaldin, et al. "Colloid supported lipid bilayers for self-assembly." Soft Matter 15 (2019): 1345-1360.

Siekmann, Britta, et al. "Preparation and structural investigations of colloidal dispersions prepared from cubic monoglyceride-water phases" International journal of pharmaceutics 244 (1-2) (Sep. 5, 2002): 33-43 (Abstract). 1 page.

Tallo Dominguez, Kirian. Colloidal lipid gels: A novel approach to structure dispersions of lipids. PhD Thesis for the University of Barcelona. May 2021. 142 pages.

Tallo, Kirian, et al. Monitoring the formation of a colloidal lipid gel at the nanoscale: vesicle aggregation driven by a temperature-induced mechanism. Journal of Materials Chemistry B, (2021), 9, pp. 7472-7481.

First Office Action for Chinese Application No. 202080086262.8 filed on Nov. 11, 2020 on behalf of Probiotical S.P.A. Issued on Sep. 13, 2023. 22 pages. Original and English Translation.

Search Report for Chinese Application No. 202080086262.8 filed on Nov. 11, 2020 on behalf of Probiotical S.P.A. Issued on Sep. 8, 2023. 4 pages. Original and English Translation.

Decision of Refusal for Japanese Patent Application No. 2022-526820 filed on Nov. 11, 2020 on behalf of Probiotical S.P.A. Mailed on May 20, 2025. Original and English summary translation. 5 pages.

Sato, Kiyotaka. Structure and Physical Properties of Lipids From the Perspective of Food Physics, Journal of the Graduate School of Biosphere Science, Hiroshima University, vol. 48, (2009), pp. 77-94. Original plus English translation. 20 pages.

Sato, Kiyotaka. "Structures and Physical Properties of Crystalline Fatty Acids and Triacylglycerols", Journal of Japan Oil Chemist's Society, (1995), vol. 44, No. 10, pp. 702-711. 13 pages. Original plus English Abstract.

Aloisio I, et al. Three-Month Feeding Integration With BifidobacteriumStrains Prevents Gastrointestinal Symptoms in Healthy Newborns. Front Nutr. (May 25, 2018);5:39. doi: 10.3389/fnut.2018.00039. PMID: 29888226; PMCID: PMC5980983.

Bordugo A, et al. Assessing Gut Microbiota in an Infant with Congenital Propionic Acidemia before and after Probiotic Supplementation. Microorganisms. (Dec. 16, 2021);9(12):2599. doi: 10.3390/microorganisms9122599. PMID: 34946200; PMCID: PMC8703847.

Boyte, Marie-Eve, et al., "Probiotic and postbiotic analytical methods: a perspective of available enumeration techniques", Frontiers in Microbiology, (Dec. 7, 2023), 14:1304621. 15 pages. Doi: 10.3389/fmicb.2023.1304621.

Bron PA, et al. Delivery of Metabolically Neuroactive Probiotics to the Human Gut. Int J Mol Sci. (Aug. 24, 2021);22(17):9122. doi: 10.3390/ijms22179122. PMID: 34502031; PMCID: PMC8431588.

Chamignon C, et al., Beneficial Effects of *Lactobacilli* Species on Intestinal Homeostasis in Low-Grade Inflammation and Stress Rodent Models and Their Implication in the Modulation of the Adhesive Junctional Complex. Biomolecules. (Aug. 24, 2023);13(9):1295. doi: 10.3390/biom13091295. PMID: 37759696; PMCID: PMC10527021.

Ciprandi G, et al. The Probiotics in Pediatric Asthma Management (PROPAM) study: A Post Hoc analysis in allergic children. Ann Allergy Asthma Immunol. (Jul. 2022) ;129(1):111-113. doi: 10.1016/j.anai.2022.04.026. (Epub Apr. 26, 2022). PMID: 35487387.

Ciprandi G, et al. The PRObiotics in Pediatric Asthma Management (PROPAM) study: A post hoc analysis in preschoolers. Pediatr Pulmonol. (May 2022) ;57(5):1355-1357. doi: 10.1002/ppul.25878. (Epub Mar. 11, 2022). PMID: 35243820.

Colombo D, et al. Probiotics and Prebiotics Orally Assumed as Disease Modifiers for Stable Mild Atopic Dermatitis: An Italian Real-Life, Multicenter, Retrospective, Observational Study. Medicina (Kaunas). (Nov. 27, 2023);59(12):2080. doi: 10.3390/medicina59122080. PMID: 38138183; PMCID: PMC10744411.

Da Silva, Thaiane Marques, et al. Viability of microencapsulated Lactobacillus acidophilus by complex coacervation associated with enzymatic crosslinking under application in different fruit juices. Food Research International, 141 (Epub: Feb. 1, 2021) 110190. 9 pages.

De Mauri A, et al. Probiotics-Supplemented Low-Protein Diet for Microbiota Modulation in Patients with Advanced Chronic Kidney Disease (ProLowCKD): Results from a Placebo-Controlled Randomized Trial. Nutrients. (Apr. 14, 2022); 14(8):1637. doi: 10.3390/nu14081637. PMID: 35458199; PMCID: PMC9025298.

Deidda F, et al. Bifidobacteria Strain Typing by Fourier Transform Infrared Spectroscopy. Front Microbiol. (Sep. 13, 2021);12:692975. doi: 10.3389/fmicb.2021.692975. PMID: 34589064; PMCID: PMC8473902.

Deidda F, et al. In-process real-time probiotic phenotypic strain identity tracking: The use of Fourier transform infrared spectroscopy. Front Microbiol. (Dec. 8, 2022);13:1052420. doi: 10.3389/fmicb.2022.1052420. PMID: 36569057; PMCID: PMC9772554.

Deidda F, et al. In Vitro Activity of Lactobacillus fermentum LF5 Against Different *Candida* Species and Gardnerella vaginalis: A New Perspective to Approach Mixed Vaginal Infections? J Clin

(56) References Cited

OTHER PUBLICATIONS

Gastroenterol. (Nov./Dec. 2016);50 Suppl 2, Proceedings from the 8th Probiotics, Prebiotics & New Foods for Microbiota and Human Health meeting held in Rome, Italy on Sep. 13-15, 2015:S168-S170. doi: 10.1097/MCG.0000000000000692. PMID: 27741167.
Deidda F, et al. New Approach in Acne Therapy: A Specific Bacteriocin Activity and a Targeted Anti IL-8 Property in Just 1 Probiotic Strain, the L. salivarius LS03. J Clin Gastroenterol. (Nov./Dec. 2018);52 Suppl 1, Proceedings from the 9th Probiotics, Prebiotics and New Foods, Nutraceuticals and Botanicals for Nutrition & Human and Microbiota Health Meeting, held in Rome, Italy from Sep. 10 to 12, 2017:S78-S81. doi: 10.1097/MCG.0000000000001053. PMID: 29782471.
017 Deidda F, et al. The In Vitro Effectiveness of Lactobacillus fermentum Against Different *Candida* Species Compared With Broadly Used Azoles. J Clin Gastroenterol. (Nov./Dec. 2016);50 Suppl 2, Proceedings from the 8th Probiotics, Prebiotics & New Foods for Microbiota and Human Health meeting held in Rome, Italy on Sep. 13-15, 2015:S171-S174. doi: 10.1097/MCG.0000000000000686. PMID: 27741168.
Del Piano M, et al. Assessment of the capability of a gelling complex made of tara gum and the exopolysaccharides produced by the microorganism *Streptococcus thermophilus* ST10 to prospectively restore the gut physiological barrier: a pilot study. J Clin Gastroenterol. (Nov./Dec. 2014);48 Suppl 1:S56-61. doi: 10.1097/MCG.0000000000000254. PMID: 25291130.
Del Piano M, et al. Can Probiotics Reduce Diarrhea and Infant Mortality in Africa?: The Project of a Pilot Study. J Clin Gastroenterol. (Nov./Dec. 2016);50 Suppl 2, Proceedings from the 8th Probiotics, Prebiotics & New Foods for Microbiota and Human Health meeting held in Rome, Italy on Sep. 13-15, 2015:S120-S123. doi: 10.1097/MCG.0000000000000677. PMID: 27741153.
Del Piano M, et al. Correlation between chronic treatment with proton pump inhibitors and bacterial overgrowth in the stomach: any possible beneficial role for selected lactobacilli? J Clin Gastroenterol. (Nov./Dec. 2014);48 Suppl 1:S40-6. doi: 10.1097/MCG.0000000000000256. PMID: 25291126.
Del Piano M., et al., "Evaluation of the Intestinal Colonization by Microencapsulated Probiotic Bacteria in Comparison With Same Uncoated Strains," Journal of clinical gastroenterology, (Sep. 2010), vol. 44 Suppl 1, 5 pages.
Del Piano M., et al., "Is Microencapsulation the Future of Probiotic Preparations? The Increased Efficacy of Gastro-protected Probiotics," Gut Microbes, (Mar. 2011), vol. 2 (2), pp. 4 pages.
Di Cesare F, et al. Exploring the Effects of Probiotic Treatment on Urinary and Serum Metabolic Profiles in Healthy Individuals. J Proteome Res. Dec. 1, 2023;22(12):3866-3878. doi: 10.1021/acs.jproteome.3c00548. (Epub Nov. 16, 2023) Nov. 16. PMID: 37970754; PMCID: PMC10696601.
Di Gioia D, et al. A prospective longitudinal study on the microbiota composition in amyotrophic lateral sclerosis. BMC Med. (Jun. 17, 2020);18(1):153. doi: 10.1186/s12916-020-01607-9. PMID: 32546239; PMCID: PMC7298784.
Di Pierro F, et al. Bifidobacterium longum W11: Uniqueness and individual or combined clinical use in association with rifaximin. Clin Nutr ESPEN. Apr. 2021;42:15-21. doi: 10.1016/j.clnesp.2020.12.025. (Epub Feb. 17, 2021). PMID: 33745570.
Di Pierro F, et al. Effects of rifaximin-resistant Bifidobacterium longum W11 in subjects with symptomatic uncomplicated diverticular disease treated with rifaximin. Minerva Gastroenterol Dietol. Dec. 2019;65(4):259-264. doi: 10.23736/S1121-421X.19.02622-9. (Epub Oct. 24, 2019). PMID: 31646852.
Drago L, et al. PROPAM Study Group. A post hoc analysis on the effects of a probiotic mixture on asthma exacerbation frequency in schoolchildren. ERJ Open Res. (May 9, 2022);8(2):00020-2022. doi: 10.1183/23120541.00020-2022. PMID: 35539434; PMCID: PMC9081543.
Drago, L. et al., The Probiotics in Pediatric Asthma Management (PROPAM) Study in the Primary Care Setting: A Randomized, Controlled, Double-Blind Trial with Ligilactobacillus salivarius LS01 (DSM 22775) and Bifidobacterium breve B632 (DSM 24706). Hindawi, Journal of Immunology Research, (Jan. 17, 2022), Article ID 3837418, 7 pages. Doi.org/10.1155/2022/3837418.
Examination report No. 1 for standard patent application for Australian patent application No. 2020381977 filed on Nov. 11, 2020. Mailed on Nov. 28, 2025. 8 pages.
Ferrari E, et al. Probiotics Supplements Reduce ER Stress and Gut Inflammation Associated with Gliadin Intake in a Mouse Model of Gluten Sensitivity. Nutrients. (Apr. 7, 2021);13(4):1221. doi: 10.3390/nu13041221. PMID: 33917155; PMCID: PMC8067866.
Filippelli M, et al. Effectiveness of oral probiotics supplementation in the treatment of adult small chalazion. Int J Ophthalmol. (Jan. 18, 2022); 15(1):40-44. doi: 10.18240/ijo.2022.01.06. PMID: 35047354; PMCID: PMC8720352.
Filippelli M, et al. Intestinal microbiome: a new target for chalaziosis treatment in children? Eur J Pediatr. Apr. 2021;180(4):1293-1298. doi: 10.1007/s00431-020-03880-5. (Epub Nov. 23, 2020). PMID: 33226501.
Foglia, Chiara et al., "New insights in enumeration methodologies of probiotic cells in finished products", Journal of Microbiological Methods, (ePub Jul. 2, 2020), 175, 105993. 6 pages.
Ghini V, et al. Effects of Probiotics Administration on Human Metabolic Phenotype. Metabolites. (Oct. 7, 2020);10(10):396. doi: 10.3390/metabo10100396. PMID: 33036487; PMCID: PMC7601401.
Graziano T, et al. The Possible Innovative Use of Bifidobacterium longum W11 in Association With Rifaximin: A New Horizon for Combined Approach? J Clin Gastroenterol. (Nov./Dec. 2016) ;50 Suppl 2, Proceedings from the 8th Probiotics, Prebiotics & New Foods for Microbiota and Human Health meeting held in Rome, Italy on Sep. 13-15, 2015:S153-S156. doi: 10.1097/MCG.0000000000000683. Erratum in: J Clin Gastroenterol. Jan. 2017;51(1):89. doi: 10.1097/MCG.0000000000000766. PMID: 27741162.
Guidetti C, et al. Randomized Double-Blind Crossover Study for Evaluating a Probiotic Mixture on Gastrointestinal and Behavioral Symptoms of Autistic Children. J Clin Med. (Sep. 6, 2022);11(18):5263. doi: 10.3390/jcm11185263. PMID: 36142909; PMCID: PMC9504504.
Himawan, C., et al., "Thermodynamic and kinetic aspects of fat crystallization," Adv. Colloid Interface Sci. 122 (1-3) (Epub Aug. 14, 2006) 3-33.
Jackson SA, et al. Improving End-User Trust in the Quality of Commercial Probiotic Products. Front Microbiol. (Apr. 17, 2019);10:739. doi: 10.3389/fmicb.2019.00739. PMID: 31105649; PMCID: PMC6499161.
Jäger R, et al. International Society of Sports Nutrition Position Stand: Probiotics. J Int Soc Sports Nutr. (Dec. 21, 2019);16(1):62. Doi: 10.1186/s12970-019-0329-0. PMID: 31864419; PMCID: PMC6925426.
Jäger R, et al. Probiotic *Streptococcus thermophilus* FP4 and Bifidobacterium breve BR03 Supplementation Attenuates Performance and Range-of- Motion Decrements Following Muscle Damaging Exercise. Nutrients. (Oct. 14, 2016);8(10):642. doi: 10.3390/nu8100642. PMID: 27754427; PMCID: PMC5084029.
Jordal PL, et al. Collaborative cytometric inter-laboratory ring test for probiotics quantification. Front Microbiol. (Nov. 10, 2023);14:1285075. doi: 10.3389/fmicb.2023.1285075. PMID: 38029213; PMCID: PMC10667725.
Lombardo D, et al. Application of Fourier transform infrared spectroscopy for real-time typing of Acinetobacter baumannii outbreak in intensive care unit. Future Microbiol. Nov. 2021;16:1239-1250. doi: 10.2217/fmb-2020-0276. (Epub Oct. 22, 2021). PMID: 34674538.
Magistrelli L, et al. Probiotics May Have Beneficial Effects in Parkinson's Disease: In vitro Evidence. Front Immunol. (May 7, 2019);10:969. doi: 10.3389/fimmu.2019.00969. PMID: 31134068; PMCID: PMC6513970.
Marangoni, A.G. (ed.), Structure-Function Analysis of Edible Fats, AOCS Press, 2nd ed., (2018), 421 pages.
Marotta A, et al. Effects of Probiotics on Cognitive Reactivity, Mood, and Sleep Quality. Front Psychiatry. (Mar. 27, 2019);10:164. doi: 10.3389/fpsyt.2019.00164. PMID: 30971965; PMCID: PMC6445894.

(56) References Cited

OTHER PUBLICATIONS

Mazzini L, et al. Potential Role of Gut Microbiota in ALS Pathogenesis and Possible Novel Therapeutic Strategies. J Clin Gastroenterol. (Nov./Dec. 2018);52 Suppl 1, Proceedings from the 9th Probiotics, Prebiotics and New Foods, Nutraceuticals and Botanicals for Nutrition & Human and Microbiota Health Meeting, held in Rome, Italy from Sep. 10 to 12, 2017:S68-S70. doi: 10.1097/MCG.0000000000001042. PMID: 29782468.

Mogna L, et al. Micronized Cells of the Probiotic Strain Bifidobacterium lactis BS01 Activate Monocyte Polarization: A New Approach. J Clin Gastroenterol. (Nov./Dec. 2018);52 Suppl 1, Proceedings from the 9th Probiotics, Prebiotics and New Foods, Nutraceuticals and Botanicals for Nutrition & Human and Microbiota Health Meeting, held in Rome, Italy from Sep. 10 to 12, 2017:S57-S61. doi: 10.1097/MCG.0000000000001068. PMID: 29864069.

Mogna L, et al. Screening of different probiotic strains for their in vitro ability to metabolise oxalates: any prospective use in humans? J Clin Gastroenterol. (Nov./Dec. 2014);48 Suppl 1:S91-5. doi: 10.1097/MCG.0000000000000228. PMID: 25291139.

Mogna L, et al. Selenium and zinc internalized by Lactobacillus buchneri Lb26 (DSM 16341) and Bifidobacterium lactis Bb1 (DSM 17850): improved bioavailability using a new biological approach. J Clin Gastroenterol. (Oct. 2012) ;46 Suppl:S41-5. doi: 10.1097/MCG.0b013e318268861d. Erratum in: J Clin Gastroenterol. Aug. 2019;53(7):551. doi: 10.1097/MCG.0000000000001241. PMID: 22955356.

Mohr AE, et al. The athletic gut microbiota. J Int Soc Sports Nutr. (May 12, 2020);17(1):24. doi: 10.1186/s12970-020-00353-w. PMID: 32398103; PMCID: PMC7218537.

Monzani R, et al. The Gut-Ex-Vivo System (GEVS) Is a Dynamic and Versatile Tool for the Study of DNBS-Induced IBD in BALB/C and C57BL/6 Mice, Highlighting the Protective Role of Probiotics. Biology (Basel). (Oct. 27, 2022);11(11):1574. doi: 10.3390/biology11111574. PMID: 36358275; PMCID: PMC9687175.

Morazzoni C, et al. Proof of concept: real-time viability and metabolic profiling of probiotics with isothermal microcalorimetry. Front Microbiol. (Jun. 19, 2024);15:1391688. doi: 10.3389/fmicb.2024.1391688. PMID: 38962141; PMCID: PMC11220157.

Moschonis G, et al. Evaluation of a probiotic blend on psychosocial health and biomarkers of inflammatory, immune and stress response in adults with subthreshold depression: a double-blind, randomised, placebo-controlled trial. Br J Nutr. (Oct. 29, 2024):1-15. doi: 10.1017/S0007114524001703. Epub ahead of print. PMID: 39468832.

Nicola S, et al. Searching for the Perfect Homeostasis: Five Strains of Bifidobacterium longum From Centenarians Have a Similar Behavior in the Production of Cytokines. J Clin Gastroenterol. (Nov./Dec. 2016);50 Suppl 2, Proceedings from the 8th Probiotics, Prebiotics & New Foods for Microbiota and Human Health meeting held in Rome, Italy on Sep. 13-15, 2015:S126-S130. doi: 10.1097/MCG.0000000000000678. PMID: 27741155. Abstract.

Nobili A, et al. Innovative Biomarkers for Obesity and Type 1 Diabetes Based on Bifidobacterium and Metabolomic Profiling. Microorganisms. (May 3, 2024);12(5):931. doi: 10.3390/microorganisms12050931. PMID: 38792760; PMCID: PMC11124356.

Orlandoni P, et al. Safety and Efficacy of Probiotic Supplementation in Reducing the Incidence of Infections and Modulating Inflammation in the Elderly with Feeding Tubes: A Pilot, Double-Blind, Placebo-Controlled Study, "IntegPRO". Nutrients. (Jan. 27, 2021);13(2):391. doi: 10.3390/nu13020391. PMID: 33513820; PMCID: PMC7911800.

Pane M, et al. Efficacy of Limosilactobacillus fermentum in the management of vulvovaginal candidiasis: comparative analysis with topical miconazole in a single-blind randomized clinical trial. Front Microbiol. (Aug. 1, 2024);15:1428590. doi: 10.3389/fmicb.2024.1428590. PMID: 39149209; PMCID: PMC11324542.

Pane M, et al. Flow Cytometry: Evolution of Microbiological Methods for Probiotics Enumeration. J Clin Gastroenterol. (Nov./Dec. 2018);52 Suppl 1, Proceedings from the 9th Probiotics, Prebiotics and New Foods, Nutraceuticals and Botanicals for Nutrition & Human and Microbiota Health Meeting, held in Rome, Italy from Sep. 10 to 12, 2017:S41-S45. doi: 10.1097/MCG.0000000000001057. PMID: 29762266. Abstract.

Pane M, et al. Gut Microbiota, Probiotics, and Sport: From Clinical Evidence to Agonistic Performance. J Clin Gastroenterol. (Nov./Dec. 2018);52 Suppl 1, Proceedings from the 9th Probiotics, Prebiotics and New Foods, Nutraceuticals and Botanicals for Nutrition & Human and Microbiota Health Meeting, held in Rome, Italy from Sep. 10 to 12, 2017: S46-S49. doi: 10.1097/MCG.0000000000001058. PMID: 29782463. Abstract.

Pyar, H and Peh, K-K (2014) "Enteric coating of granules containing the probiotic Lactobacillus acidophilus," Acta Pharmaceutica, 64(2) (2014): 247-256, doi:10.2478/acph-2014-0011.

Rinaldi F, et al. Facial Acne: A randomized, Double-Blind, Placebo-Controlled Study on the Clinical Efficacy of a Symbiotic Dietary Supplement. Dermatol Ther (Heidelb). Feb. 2022;12(2):577-589. doi: 10.1007/s13555-021-00664-z. (Epub Jan. 21, 2022). PMID: 35061237; PMCID: PMC8850513.

Rouanet A, et al. Live Biotherapeutic Products, A Road Map for Safety Assessment. Front Med (Lausanne). (Jun. 19, 2020);7:237. doi: 10.3389/fmed.2020.00237. PMID: 32637416; PMCID: PMC7319051.

Sato, K. & S. Ueno, "Crystallization, transformation and microstructures of polymorphic fats in colloidal dispersion states", Curr. Opin. Colloid Interface Sci., vol. 16, Issue 5, (Oct. 2011) 384-390.

Sato, K. "Crystallization behaviour of fats and lipids—a review," Chem. Eng. Sci. 56 (Apr. 2001) 2255-2265.

Solito A, et al. Supplementation with Bifidobacterium breve BR03 and B632 strains improved insulin sensitivity in children and adolescents with obesity in a cross-over, randomized double-blind placebo-controlled trial. Clin Nutr. Jul. 2021;40(7):4585-4594. doi: 10.1016/j.clnu.2021.06.002. (Epub Jun. 11, 2021). PMID: 34229263.

Spacova I, et al. Comparing technology and regulatory landscape of probiotics as food, dietary supplements and live biotherapeutics. Front Microbiol. (Dec. 19, 2023);14:1272754. doi: 10.3389/fmicb.2023.1272754. PMID: 38188575; PMCID: PMC10770255.

Squarzanti DF, et al. An animal derivative-free medium enhances Lactobacillus johnsonii LJO02 supernatant selective efficacy against the methicillin (oxacillin)-resistant *Staphylococcus aureus* virulence through key-metabolites. Sci Rep. (May 23, 2022);12(1):8666. doi: 10.1038/s41598-022-12718-z. PMID: 35606510; PMCID: PMC9126979.

Tierney BT, Functional response to a microbial synbiotic in the gastrointestinal system of children: a randomized clinical trial. Pediatr Res. (Jun. 2023) ;93(7):2005-2013. doi: 10.1038/s41390-022-02289-0. (Epub: Nov. 2, 2022). PMID: 36319696; PMCID: PMC10313516.

Vallino L, et al. Cell-free Lactiplantibacillus plantarum OC01 supernatant suppresses IL-6-induced proliferation and invasion of human colorectal cancer cells: Effect on β-Catenin degradation and induction of autophagy. J Tradit Complement Med. (Feb. 21, 2023);13(2):193-206. doi: 10.1016/j.jtcme.2023.02.001. PMID: 36970462; PMCID: PMC10037073.

Visciglia, A. et al., "Assessment of shelf-life and metabolic viability of a multi-strain symbiotic using standard and innovative enumeration technologies", Frontiers in Microbiology, (Nov. 4, 2022), 13: 989563. 8 pages. Doi: 10.3389/fmicb.2022.989563.

Walden KE, et al. A randomized controlled trial to examine the impact of a multi-strain probiotic on self-reported indicators of depression, anxiety, mood, and associated biomarkers. Front Nutr. (Aug. 31, 2023);10:1219313. doi: 10.3389/fnut.2023.1219313. Erratum in: Front Nutr. Nov. 21, 2023;10:1324536. doi: 10.3389/fnut.2023.1324536. PMID: 37720373; PMCID: PMC10501394.

Walden KE, et al. Corrigendum: A randomized controlled trial to examine the impact of a multi-strain probiotic on self-reported indicators of depression, anxiety, mood, and associated biomarkers. Front Nutr. (Nov. 21, 2023); 10:1324536. doi: 10.3389/fnut.2023.1324536. (Erratum for: Front Nutr. Aug. 31, 2023;10:1219313. doi: 10.3389/fnut.2023.1219313. PMID: 38075220; PMCID: PMC10698864).

Weitzel, M.L. Jane, et al., "Improving and Comparing Probiotic Plate Count Methods by Analytical Procedure Lifecycle Manage-

(56) References Cited

OTHER PUBLICATIONS ment", Frontiers in Microbiology, (Jul. 12, 2021), 12: 693066. 17 pages. Doi: 10.3389/fmicb.2021.693066.

Zanetta P, et al. Growth Conditions Influence Lactobacillus Cell-Free Supernatant Impact on Viability, Biofilm Formation, and Co-Aggregation of the Oral Periodontopathogens Fusobacterium nucleatum and Porphyromonas gingivalis. Biomedicines. (Mar. 11, 2023);11(3):859. doi: 10.3390/biomedicines11030859. PMID: 36979838; PMCID: PMC10045872.

Zanetta P, et al. In Vitro Selection of Lactobacillus and Bifidobacterium Probiotic Strains for the Management of Oral Pathobiont Infections Associated to Systemic Diseases. Int J Mol Sci. (Dec. 18, 2022);23(24):16163. doi: 10.3390/ijms232416163. PMID: 36555802; PMCID: PMC9787750.

Zanetta P et al. Lactobacillus johnsonii LJO02 (DSM 33828) Cell-Free Supernatant and Vitamin D Improve Wound Healing and Reduce Interleukin-6 Production in *Staphylococcus aureus*-Infected Human Keratinocytes. Pharmaceutics. (Dec. 21, 2023);16(1):18. doi: 10.3390/pharmaceutics16010018. PMID: 38276496; PMCID: PMC10820395.

Zanetta P, et al. Probiotics as Potential Biological Immunomodulators in the Management of Oral Lichen Planus: What's New? Int J Mol Sci. (Mar. 23, 2022);23(7):3489. doi: 10.3390/ijms23073489. PMID: 35408849; PMCID: PMC8998608.

Del Piano, M. et al. Is microencapsulation the future of probiotic preparations the increased efficacy of gastro-protected probiotics. (2011) (Publication).

Midori Gotoh, Crystal Structures and Polymorphism of Normal Saturated Fatty Acids, Journal of Japan Oil Chemist's Society, (1987), vol. 36, No. 12, pp. 909-919. Original and Machine Translation.

Pre-appeal Examination Report for Japanese Application No. JP2022526820. Dated Sep. 12, 2025. English only. 2 pages.

Satoshi Ueno et al., Delicious Physics of Chocolate, J. Phys. Soc. Jpn., (2016), vol. 71, No. 11, pp. 767-770. Original and machine translation.

* cited by examiner

GRANULAR BACTERIA GASTROPROTECTED WITH A COATING MATRIX IN CRYSTALLINE FORM, PROCESS FOR THE PREPARATION THEREOF AND COMPOSITIONS THEREOF

The present invention relates to crystalline gastroprotected granular bacteria, such as bacterial strains in granular form coated with a lipid coating matrix preferably in a reduced amount, said lipid coating matrix having a crystalline form. Furthermore, the present invention relates to a process for the preparation of said crystalline gastroprotected granular bacteria. Lastly, the present invention relates to a composition comprising said crystalline gastroprotected granular bacteria.

Probiotic bacterial strains are defined as "live microorganisms which when administered in adequate amounts confer a health benefit on the host". In order to carry out their beneficial action, viable bacterial strains present in probiotic products or in Live Biotherapeutic Products (LBP) (pharmaceuticals comprising viable bacterial strains), once ingested orally, must pass through the gastric region and reach the intestine in a viable state, in order to colonise the intestine and perform their function. In order to protect bacterial strains from the acid pH environment of the stomach, it is known to coat bacterial strains with gastroprotective matrices of various kinds, such as for example lipid coating matrices.

In order to carry out their beneficial action, probiotic or viable bacterial strains must also remain effective throughout the shelf-life of the product until the time of consumption. Stability is mainly impaired by temperature and humidity and therefore an ideal control of the former and a protection from the latter can help in maintaining the probiotic or viable bacterial strain in optimal conditions to perform the complete effectiveness.

Marino et al, Journal of Functional Foods, 35 (2017) reports a study on the impact of an emulsified structure comprising saturated monoglycerides on the viability of probiotics during cold storage for up to 56 days. This document describes the preparation of a probiotic *Lactobacillus rhamnosus*, initially freeze-dried and then mixed with a liquid mixture comprising a lipid phase (sunflower oil), an aqueous phase and a monoglyceride (MG)-co-surfactant (CO). However, bacterial strains are freeze-dried but not granular. Furthermore, the process as used involves the use of liquid mixtures which may damage the viability and/or functionality of the bacteria.

Document CN 109480038 describes a method for producing temperature-resistant products comprising probiotics and chocolate. However, this document does not describe bacteria in granular form having a coating with lamellar crystalline structure nor does it describe a process capable of obtaining such coating without damaging the viability of the bacteria.

However, gastroprotection processes may cause, for various reasons, a decrease in the viability and/or functionality of the coated bacterial strains. For example, tempering by heating a lipid coating matrix (or maturation of fat) generally causes a decrease in the viability and/or functionality of the bacterial strains given that the bacterial strains are thermolabile.

The technical problem addressed and solved by the present invention lies in providing a process (in short process of the invention) for the preparation of bacterial strains, both for probiotic products and for Live Biotherapeutic Products (LBP), gastroprotected with a coating matrix that entails a low mortality of bacterial cells (i.e. maintaining membrane integrity), and, thus, maintains the viability and functionality that said cells have prior to the gastroprotection process. At the same time, the technical problem addressed by the present invention lies in providing, by means of said process of the invention, bacterial strains, or compositions containing them (probiotic products or LBP), with a high count of viable and functional bacteria, wherein said coating matrix exerts an efficient gastroprotection and/or protection from residual humidity in the finished product form and/or increase in humidity due to primary packaging materials not totally impermeable to humidity anchor after opening the package with inevitable exposure to environmental humidity.

In the light of the technical problem outlined above and following an intense research and development phase, in the present invention the Applicant provides a process (gastroprotection process, in short, process of the invention) essentially comprising the steps of (I) granulating the "bare" (not coated) bacterial strains to obtain granular bacterial strains, (II) coating said granular bacterial strains with a lipid coating matrix, preferably in a reduced amount, to obtain gastroprotected granular bacterial strains as such (or bare or not coated), and (III) tempering (or maturation) said gastroprotected granular bacterial strains as such to obtain granular bacteria gastroprotected with a coating matrix in crystalline form, as reported hereinafter and claimed in the present claims.

In the context of the present invention, the term "as such" or" bare or "not coated", per se with reference to bacterial strains or to granular bacterial strains are synonyms and can be used interchangeably. All these terms refer to not coated or non-microencapsulated bacterial strains or granulated bacterial strains.

Bacteria in granular form gastroprotected with a lipid coating matrix in crystalline form, having an amount of viable and functional bacterial cells almost unchanged with respect to the amount present prior to the gastroprotection process (process low mortality), are provided through the method of the invention.

In other words, the process of the invention allows the bacteria to granulate, coat and temper the bacteria without causing cell mortality, evaluated—for example—by means of flow cytometry (or flow cytofluorometry).

Advantageously, the process according to the present invention is carried out in the absence of solvents and/or aqueous phases in each step thereof. The absence of solvents and/or aqueous phases allows to obtain almost zero mortality of the bacterial strains.

The lower, or almost zero, mortality of the bacterial strains during the coating process of the invention, in the granulation step, in the coating step and in the tempering step, allows to preserve the viability and functionality thereof and, thus, to prepare products (compositions) containing said crystalline gastroprotected bacterial strains with a high count of viable and functional bacteria and, thus, to have processes for the preparation of gastroprotected bacteria and cost-effective products containing them.

Advantageously, the crystalline structure of the lipid coating matrix, obtained thanks to the presence of the tempering step in the process of the invention, confers to the gastroprotected granular bacteria and to the products containing said bacteria a greater resistance to the delivery of the active ingredient (i.e. probiotic or viable bacteria), which is equivalent both to a higher gastro-resistance thereof once administered through oral route and to a high stability over time (i.e. long shelf-life, long-term stability of the count).

Advantageously, the crystalline laminar structure of the lipid coating allows to obtain a coating structure having a more stable structure in terms of gastroresistance and in terms of resistance to humidity and temperature during storage (shelf life).

In addition, the crystalline structure of the lipid coating matrix, conferring greater resistance to the delivery of the active ingredient (i.e. probiotic or viable bacteria), enhances a prolonged delivery of the active ingredient into the intestine over time.

In the present context, the expression laminar structure is used to indicate a spatial configuration of the lipids corresponding to the molecular structure in lamellae, with the lipid chains more or less perpendicular to the plane of the lamellae.

In the present context, lateral structure refers to the 2D structure of molecules within a lamella.

The presence of the Bragg peaks indicates a long-range lamellar order and it allows to calculate the pitch of the lamella.

Different types of lateral organization can coexist within a lamellar structure, for example fluid and crystalline with one or more types of packing.

Advantageously, the process according to the present invention allows to obtain a lipid coating structure having a lamellar structure with crystalline structure. This is reflected in a more stable structure in terms of gastroresistance and in terms of resistance to humidity and temperature.

Lastly, the process of the invention is preferably carried out using a coating matrix comprising a reduced amount of lipids as defined in the present invention, preferably lipids of plant origin, by providing gastroprotected bacteria and products comprising said gastroprotected bacteria which fall within the limits set by regulations for the consumption of products by humans, in particular for paediatric products.

Lastly, the bacteria, the composition, the mixture and the process of the invention are easy to prepare and cost-effective.

These and other objects which will be clearer from the detailed description that follows, are achieved by the bacterial strain, by the compositions and by the mixtures of the present invention thanks to the technical characteristics claimed in the attached claims.

FIGURES

Figure 2:
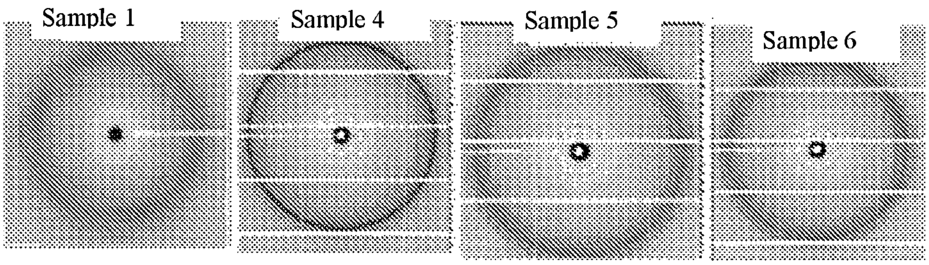
Figure 3:
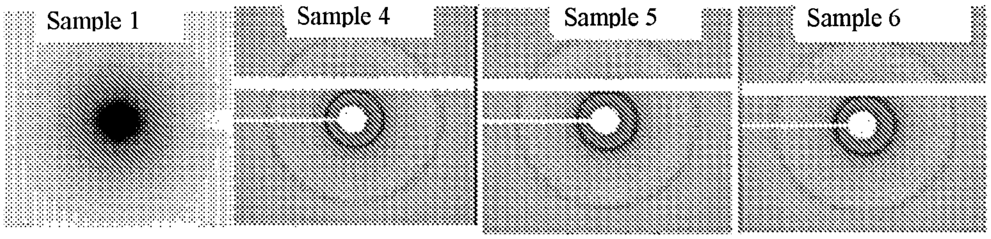
Figure 4:
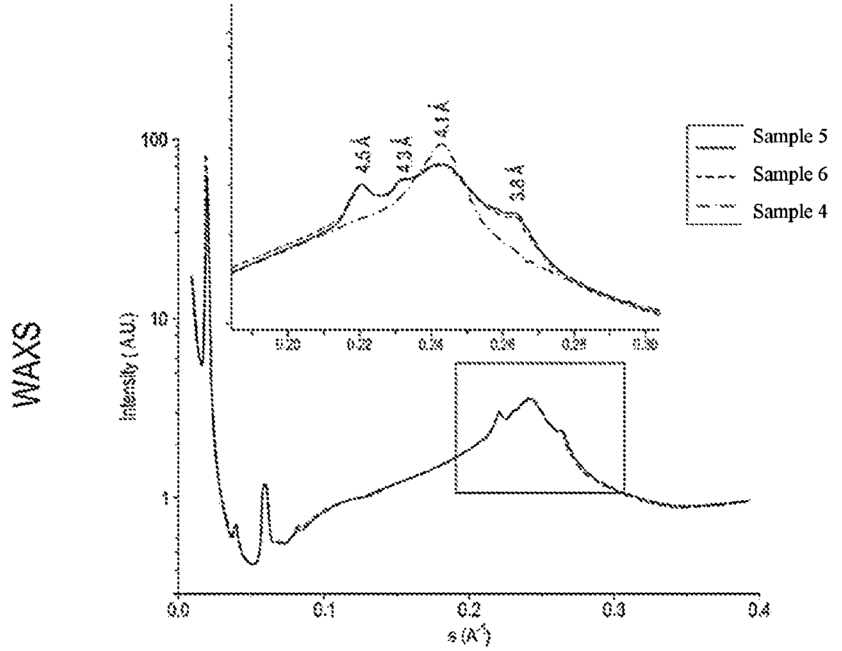
Figure 5:
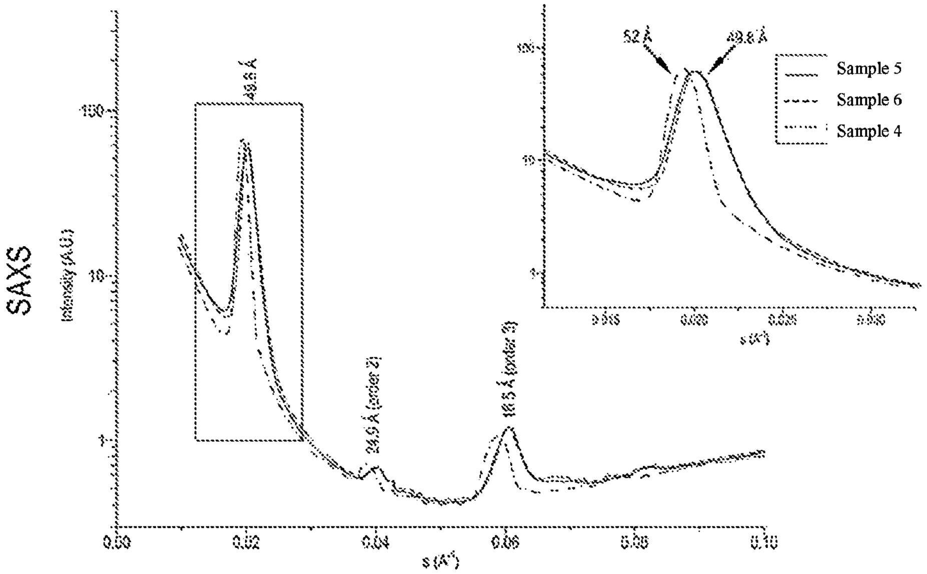
Figure 6:
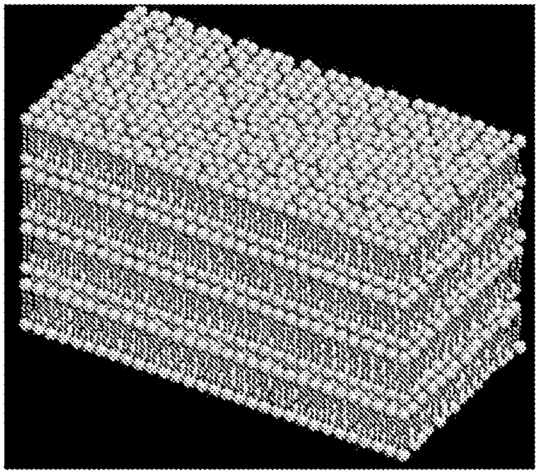
Figure 7:
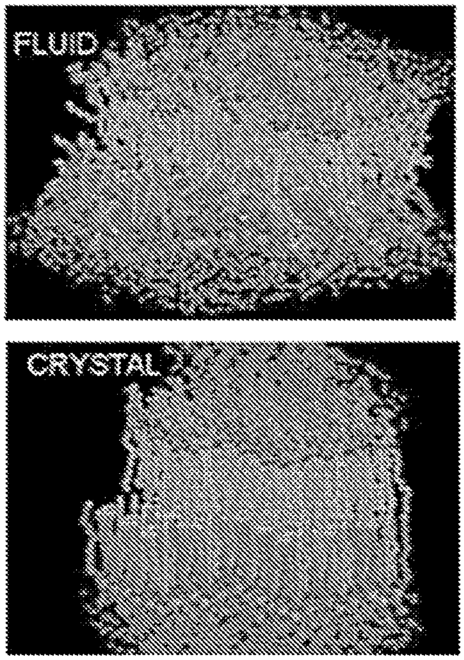
Figure 8:
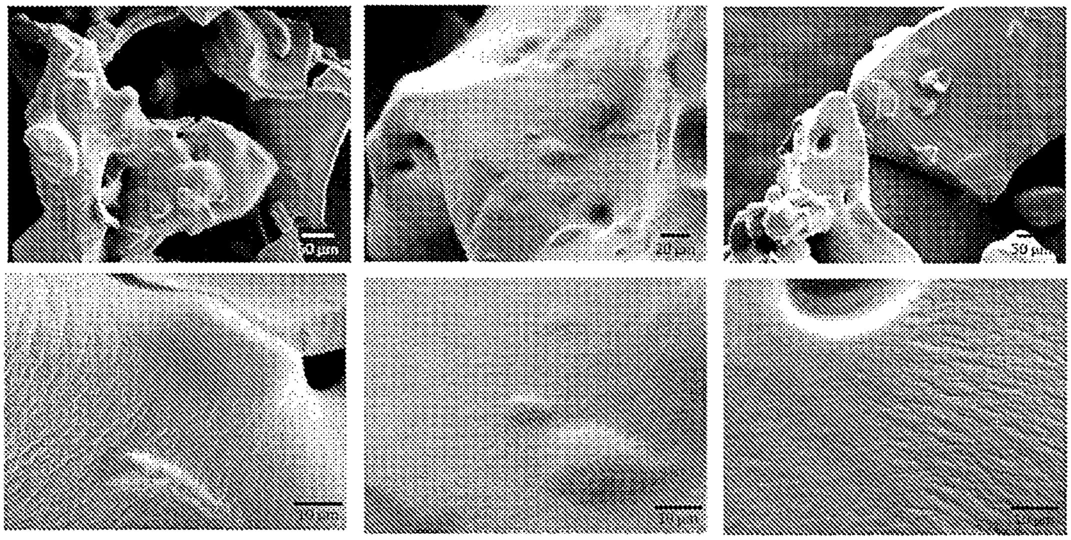
Figure 9:
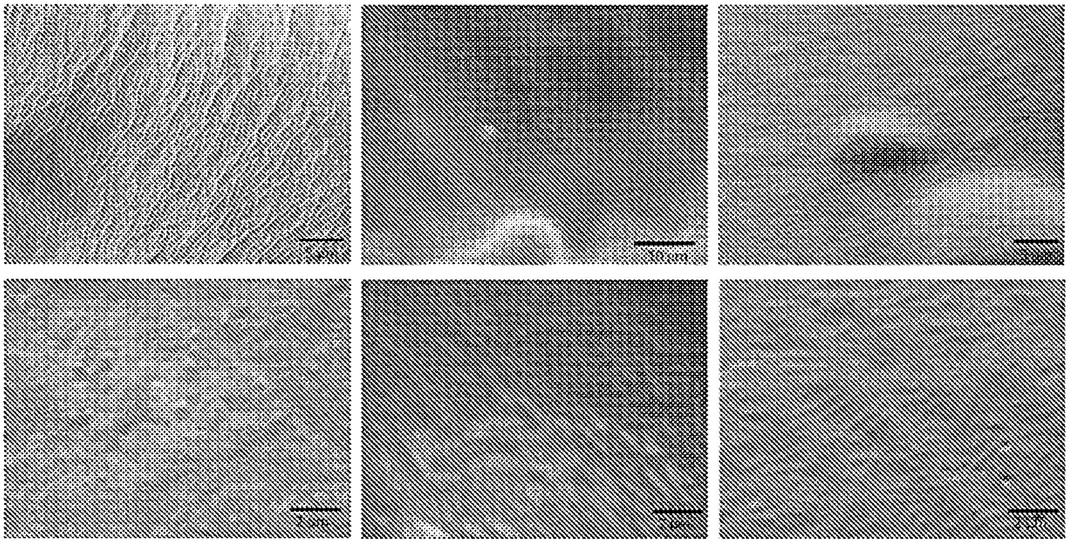
Figure 10:
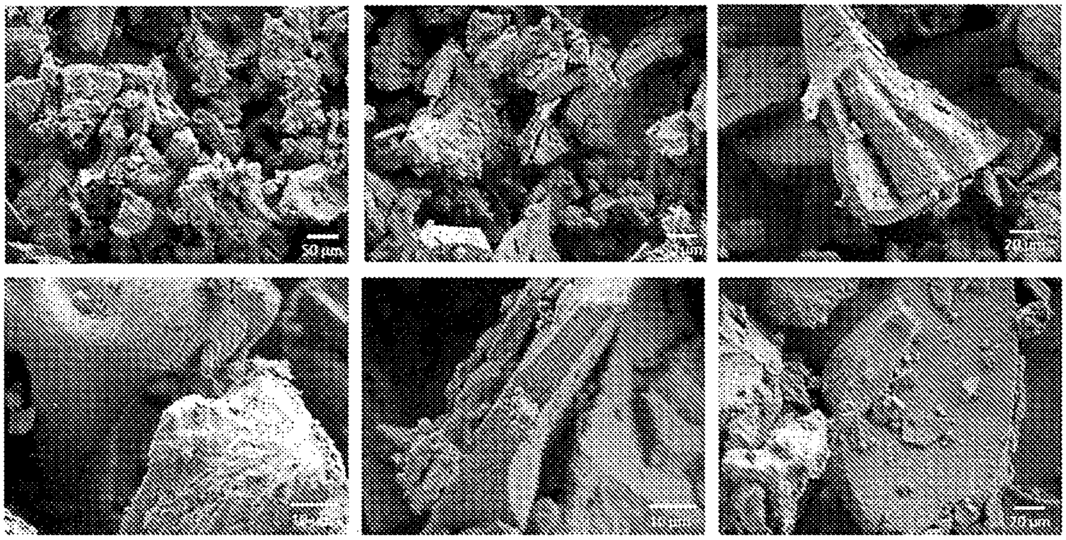
Figure 11:
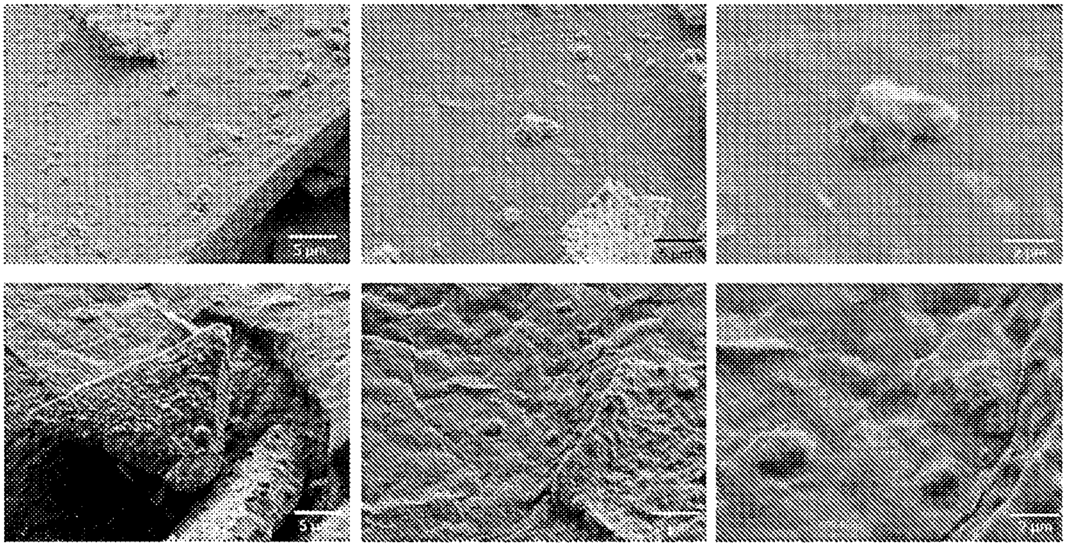
Figure 12:
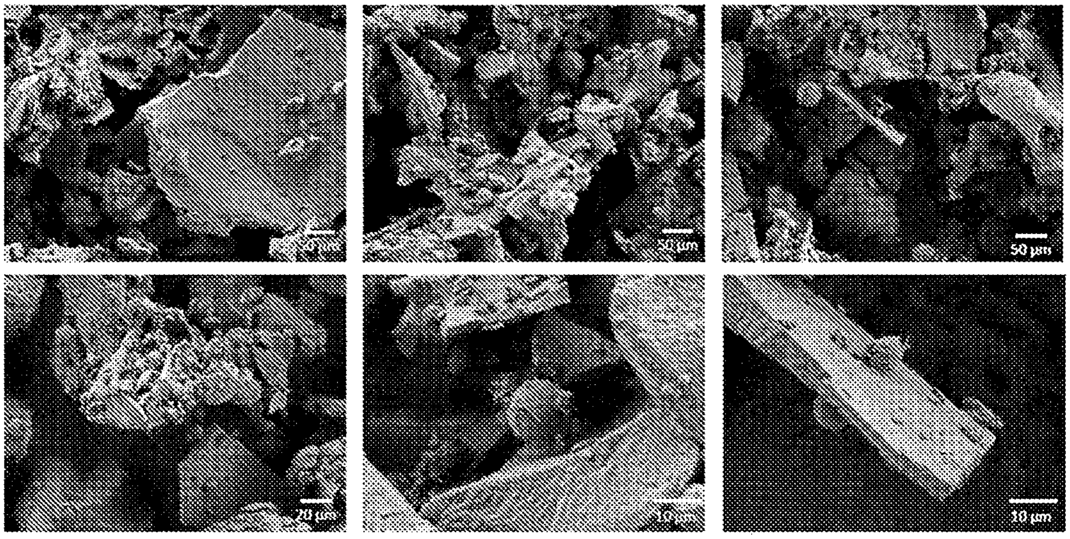
Figure 13:
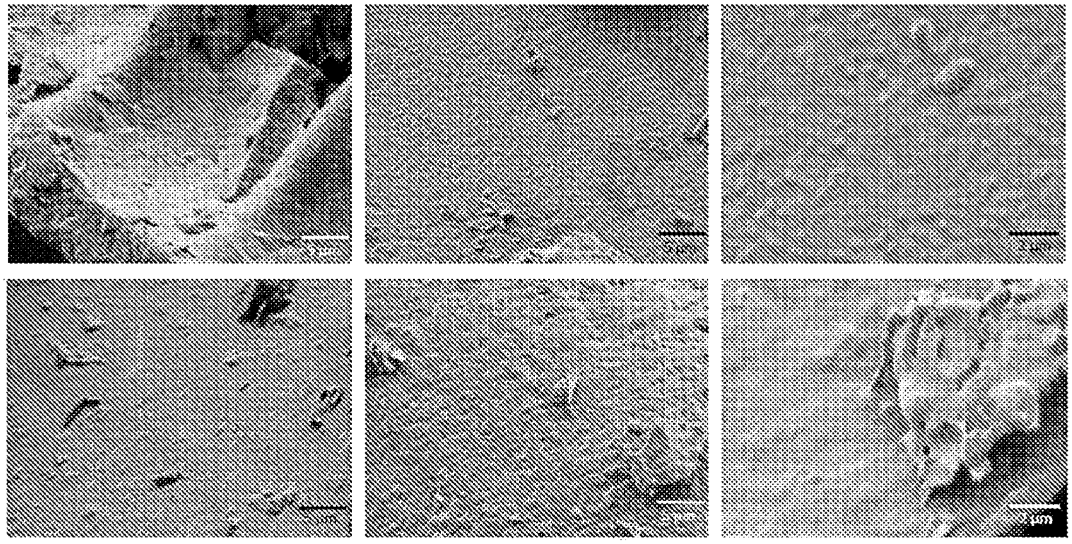
Figure 14:
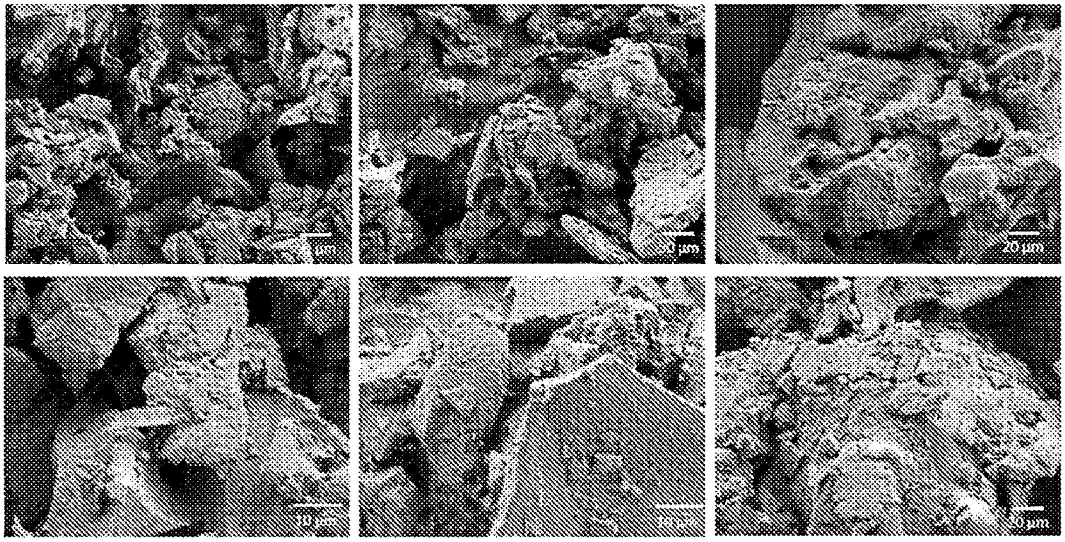
Figure 15:
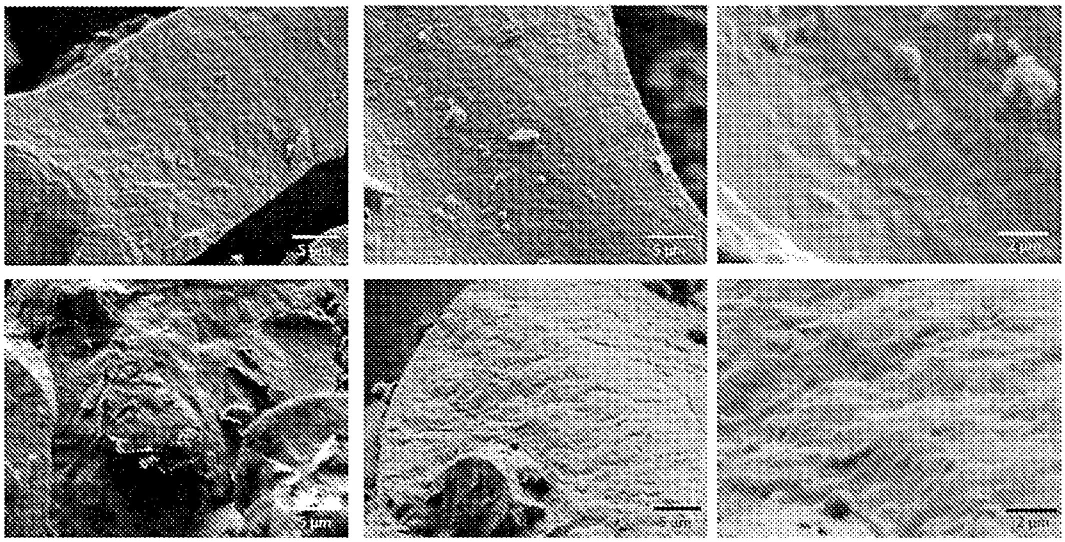

FIG. 1: schematic representation of X-ray diffraction analysis;

FIG. 2: WAXS images of the samples tested;

FIG. 3: SAXS images of the samples tested;

FIGS. 4 and 5: WAXS and SAXS analysis pattern charts of the samples tested;

FIG. 6: representation of a spatial configuration of lipids in "lamellar phase";

FIG. 7: representation of lipid lamellae with fluid or crystalline structure;

FIGS. 8-15: SEM images of the samples tested; In detail, FIGS. 8-9 are SEM images of sample 1 at different magnifications. FIGS. 10-11 are SEM images of sample 4 at different magnifications. FIGS. 12-13 are SEM images of sample 5 at different magnifications. FIGS. 14-15 are SEM images of sample 6 at different magnifications.

Figure 16:
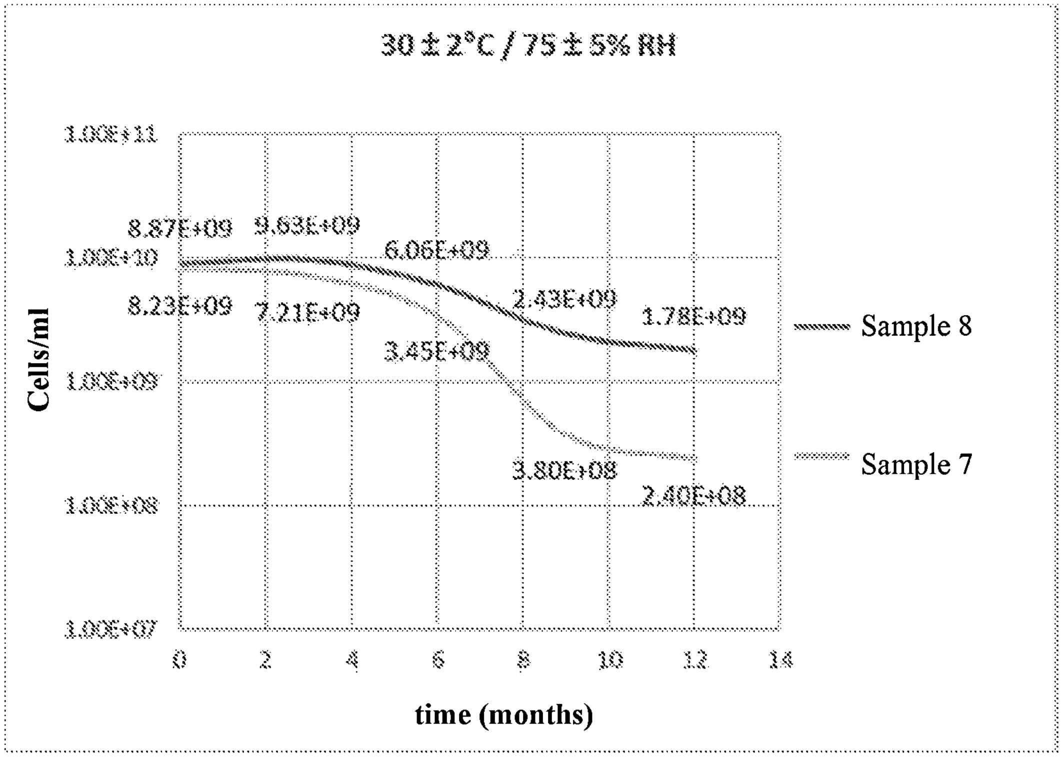
Figure 17:
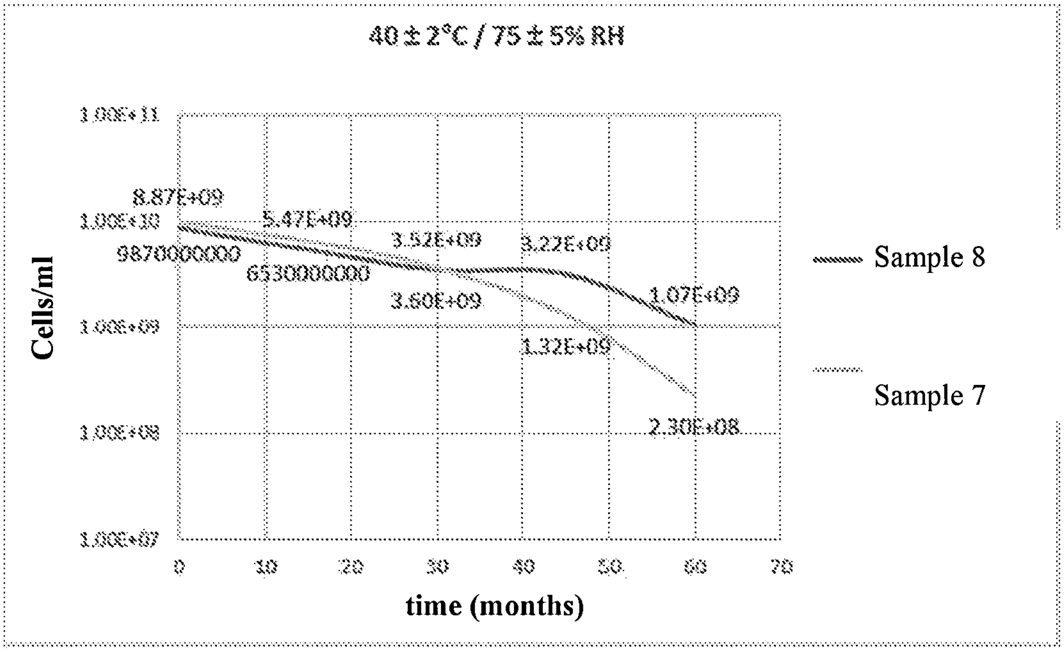

FIG. 16: measurement of the viability of the bare bacterial strain in vegetable oil and of the coated bacterial strain according to the present invention in vegetable oil at controlled temperature and humidity (30° C.-75% RH) for a time range comprised from 0 to 12 months;

FIG. 17: measurement of the viability of the bare bacterial strain in vegetable oil and of the coated bacterial strain according to the present invention in vegetable oil at controlled temperature and humidity (40° C.-75% RH) for a time range comprised from 0 to 60 days.

DETAILED DESCRIPTION OF THE INVENTION

Forming an object of the present invention are granular bacteria gastroprotected with a coating matrix with crystalline structure (in short, crystalline gastroprotected granular bacteria of the invention or bacteria of the invention), wherein said bacteria belong to at least one strain or to a mixture of strains of bacterial cells (probiotic or viable bacteria) belonging to the genera and to the species as described in the present invention, wherein said coating matrix comprises or, alternatively, consists of at least one lipid, preferably of plant origin, as described in the present invention, and wherein said at least one lipid preferably has a lamellar configuration with crystalline structure, more preferably a multilayer crystalline structure-like lamellar configuration.

Furthermore, forming an object of the present invention are granular bacteria gastroprotected with a coating matrix with crystalline structure, wherein said coating matrix comprises or, alternatively, consists of at least one lipid, wherein said at least one lipid has a lamellar configuration with crystalline structure, preferably a multilayer crystalline structure-like lamellar configuration.

In the context of the present invention the terms bacteria, bacterial strains, bacterial cells and bacterial strain cells are synonyms and used interchangeably.

In the context of the present invention, the terms gastroprotected, coated, covered are synonyms and used interchangeably.

These terms indicate that the bacteria are coated with a cover that allows to obtain protection of the bacterial strains from the acidic environment of the stomach.

Said at least one lipid, preferably of plant origin, is selected from the group A comprising or, alternatively, consisting of:

- mono-, di- or tri-glycerols esterified with saturated or unsaturated fatty acids (preferably monounsaturated), preferably esterified with saturated fatty acids (i.e. monoglycerides, diglycerides and/or triglycerides), more preferably mono- and di-glycerols esterified with saturated fatty acids with a number of carbon atoms comprised in the range from C16-C18 and/or mono-, di- or tri-glycerols esterified with saturated fatty acids with a number of carbon atoms comprised in the range from C16-C22;
- free saturated fatty acids;
- free unsaturated fatty acids, preferably mono-unsaturated;
- mono-alcohols esterified with saturated or unsaturated fatty acids (preferably monounsaturated), preferably esterified with saturated fatty acids;
- di-alcohols esterified with saturated or unsaturated fatty acids (preferably monounsaturated), preferably esterified with saturated fatty acids;
- sucrose fatty acid esters (alternatively called sucresters), preferably mixtures of mono- di- or tri-sucrose fatty acid esters, more preferably sucrose esters mainly of stearic acid and/or palmitic acid;

wherein said saturated or unsaturated fatty acids, both free and esterified with glycerol or mono-alcohols or di-alcohols or sucrose, have a number of carbon atoms comprised in the range from C6 to C32, preferably from C12 to C28, more preferably from C14 to C24, for example C16, C18, C20 and/or C22.

In the present invention, the terms sucrose fatty acid esters or saccharide esters or sucresters are synonyms and used interchangeably. Said sucrose esters are preferably mixtures of mono-, di- and/or tri-fatty acid esters, preferably fatty acids having a number of carbon atoms comprised in the range from C6 to C32, preferably from C12 to C28, more preferably from C16 to C18, such as stearic acid ($C_{18}H_{36}OR_2$) and/or palmitic acid ($C_{16}H_{32}OR_2$). The sucresters are obtained from the esterification of the fatty acids or from the trans-esterification of the methyl fatty acid esters with sucrose. The chemical-physical properties of sucresters depend on the number and on the type of esterified fatty acids.

In an embodiment of the invention, said at least one lipid is a free saturated fatty acid, preferably of plant origin, and it is selected from saturated fatty acids having a melting point comprised in the range from 35° C. to 85° C., preferably from 45° C. to 70° C., more preferably from 50° C. to 60° C.

In a preferred embodiment of the invention, said at least one lipid is selected from the group B (subgroup of group A) comprising or, alternatively, consisting of:

lipid (I): glyceryl dipalmitostearate E471, associated for example with CAS No 85251-77-0 (or 1323-83-7), EINECS: 286-490-9 (or 215-359-0), REACh (EC) no 1907/2006: exempted (food), IUPAC name "glycerides, C16-C18 mono-di-", INCI (PCPC): glyceryl distearate; example of commercial product Biogapress Vegetal BM297 ATO manufactured by Gattefossé SAS (E471); physical state: powder; melting point range: 53.00-58.00° C.; boiling point: >250.0° C.; flash point: >200.0° C.; ignition temperature (autoignition): >350.00° C.;

lipid (ii): glyceryl palmitostearate E471/gras, associated for example with CAS No 85251-77-0 (or 31566-31-1 or 123-94-4); EINECS: 286-490-9 (or 250-705-4 or 204-664-4); REACh (EC) no 1907/2006 01-2119495562-30-0014, IUPAC name "glycerides, C16-C18 mono-di-", INCI (CTFA): glyceryl stearate; example of commercial product GELEOL N MB manufactured by Gattefossé SAS; physical state: solid; flash point: >200.0° C. DIN 51376; ignition temperature (autoignition): >350.00° C.; vapour pressure: at 20.00° C. 0.0100 mbar (in short, lipid (ii));

lipid (iii): glyceryl dibehenate E471/GRAS, associated with CAS No: 77538-19-3 (or 91052-55-0) (or 30233-64-8) (or 94201-62-4), EINECS: 278-717-5 (or 293-216-1) (or 250-097-0) (or 303-650-6), REACh (EC) no 1907/2006: exempted (food), IUPAC name "glycerides, C16-22 mono-, di- and tri-", INCI (PCPC): glyceryl behenate; physical state: powder; flash point: >200.0° C.; ignition temperature (autoignition): >350.00° C.; vapour pressure: at 20.00° C. 0.0100 mbar; example of commercial product COMPRITOL E ATO or COMPRITOL E ATO FPF manufactured by Gattefossé SAS;

lipid (iv): sucresters or mixture of sucrose fatty acid esters E-473, having the following composition: mono-, di- and tri-esters not less than 80.0% (of which: sucrose monopalmitate about 55%, sucrose dipalmitate about 20%, sucrose monostearate about 13%, sucrose distearate about 5%, others <10%), free sugars not exceeding 4.0%, free fatty acids not exceeding 3% (of which: palmitic acid about 75%, stearic acid about 20%, other fatty acids about 5%), fatty acid/carbohydrate composition about 1/1, preferably about 52/48, % by weight with respect to the total weight of lipid (iv); example of commercial product Ryoto Sugar ester P-1570 manufactured by Mitsubishi Kagaku-Foods Corporation, Japan;

lipid (v): sucresters or mixture of sucrose fatty acid esters having the following composition: mono-, di- and tri-esters not less than 80.0% (of which: sucrose monostearate about 15%, sucrose distearate about 22%, sucrose tristearate about 20%, sucrose dipalmitate about 10%, sucrose polystearate about 30%, other q.s. at 100% respectively identified with CAS Nos. 25168-73-4, 27195-16-0, 27923-63-3 and 25637-97-2, and EINECS: 246-705-9, 248-317-5, 248-731-6 and 247-147-9), free sugars not exceeding 4.0%, free fatty acids not exceeding 3% (of which: stearic acid about 90%, other fatty acids About 10%), fatty acid/carbohydrate composition about 60/40, % by weight with respect to the total weight of the lipid (v); example of commercial product Ryoto Sugar Ester S-370 manufactured by Mitsubishi Kagaku-Foods Corporation, Japan, having the following characteristics: physical state: powder; melting point: from 51° C. (start) to 58° C. and 69° C. (maximum) (DSC); decomposition point: 238° C.; ignition temperature (autoignition): about. 392° C./200° C. (SETA); specific gravity: about. 0.46; or example of a commercial product SURFHOPE SE COSME C-1803 manufactured by Mitsubishi Kagaku-Foods Corporation, Japan, having the following characteristics: physical state: powder; melting point: from 51° C. (start) to 61° C. (maximum) (DSC); decomposition point: 260° C.; ignition temperature (autoignition): About 224° C.; specific gravity: about 0.46; -lipid (vi) polyglyceryl-6-distearate (or hexaglycerol diester and stearic acid) E475, identified with CAS No 34424-97-0, INCI name: polyglyceryl-6-distearate, molecular formula $C_{54}H_{106}O_{15}$; example of commercial product Plurol® Stearique WL 1009 manufactured by Gattefossé SAS (in short, lipid (vi));

d mixtures thereof.

In an alternative embodiment, said lipid group B comprises or, alternatively, consists of: said lipid (i), lipid (ii), lipid (iii), lipid (iv) and lipid (v).

In a preferred embodiment of the invention, said at least one lipid, preferably of plant origin, is selected from the group B1 (subgroup of group B) comprising or, alternatively, consisting of: said lipid (i), said lipid (ii), said lipid (iii), and mixtures thereof. Alternatively, said group B1 comprises or, alternatively, consists of: said lipid (i), said lipid (iii) and mixtures thereof; or, said group B1 comprises or, alternatively, consists of: said lipid (ii), said lipid (iii) and mixtures thereof.

In a preferred embodiment of the invention, said at least one lipid, preferably of plant origin, is selected from the group B2 (subgroup of group B) comprising or, alternatively, consisting of: said lipid (iv), said lipid (v) and mixtures thereof.

In an embodiment of the invention, said at least one lipid comprises at least one first lipid, wherein said first lipid is a mono-, di- or tri-glycerol esterified with saturated or unsaturated fatty acids (e.g. monounsaturated), preferably saturated fatty acids (i.e. monoglycerides, diglycerides or triglycerides), more preferably saturated fatty acids with a number of carbon atoms comprised in the range from C6 to C32, preferably C14 to C24, more preferably C16, C18, C20 and/or C22; and further comprises at least one second lipid, wherein said second lipid is a sucrose fatty acid ester (sucrester) as defined in the present invention, preferably a mixture of mono-, di- or tri-sucrose fatty acid esters; wherein said fatty acids esterified with glycerol or with the sucrose have a number of carbon atoms comprised in the range from C6 to C32, preferably from C14 to C24, more preferably C16, C18, C20 and/or C22.

Advantageously, said at least one lipid comprises at least one first lipid selected from said group B1 comprising or, alternatively, consisting of: said lipid (i), said lipid (ii), said lipid (iii) and mixtures thereof; and it further comprises at least one second lipid selected from said group B2 comprising or, alternatively, consisting of: said lipid (iv), said lipid (v) and mixtures thereof. For example said lipid comprises the following lipids: (i) and (iv) or (i) and (v) or (ii) and (iv) or (ii) and (v) or (iii) and (iv) or (iii) and (v) or (i) and (ii) and (iv) or (i) and (ii) and (v) or (i) and (iii) and (iv) or (i) and (iii) and (v) or (ii) and (iii) and (iv) or (ii) and (iii) and (v) or (i) and (iv) and (v) or (ii) and (iv) and (v) or (iii) and (iv) and (v).

The initials E471, E473 and E476 indicates that the respective glycerites or sucresters are food additives allowed by the European Union legislation and regulated by the Italian Ministerial Decree (D.M.1996).

It is understood that said lipid, preferably of plant origin, comprised in the coating matrix will be selected according to the intended use of the bacteria or composition of the invention, the chemical-physical nature of further components optionally comprised in the coating matrix and the additives and/or excipients optionally comprised in the composition of the invention, of the physical state of the composition of the invention.

Advantageously, the granular bacteria gastroprotected with a coating matrix with crystalline structure according to the invention comprise, or alternatively, consist of (a) bacteria (bacteria as such or bare or not coated) in a % by weight comprised in the range from 60% to 90% and of (b) said coating matrix comprising or, alternatively, consisting of said at least one lipid, according to the various embodiments reported in the present description (lipids of group A, preferably lipids of group B, more preferably the lipid of group B1 or the lipids of group B1 in association with the lipids of group B2 according to the examples reported in the present invention), in a % by weight comprised in the range from 10% to 40%, with respect to the total weight of the gastroprotected granular bacteria; preferably the bacteria from 65% to 85% and the coating matrix from 15% to 35%; more preferably the bacteria from 70% to 80% and the coating matrix from 20% to 30%.

The bacteria subject of the present invention, such as bacteria of the invention, bacteria of the invention comprised in the composition of the invention and bacteria of the invention obtained by the process of the invention, comprise or, alternatively, consist of at least one bacterial cell strain or a mixture of different bacterial cell strains. Said at least one strain or mixture of bacterial cell strains belongs to or belong to one or more families selected from the group comprising or, alternatively, consisting of: *Firmicutes, Actibacteria, Bacteroidetes, Proteobacteria*, and mixtures thereof. Said at least one strain or mixture of bacterial cell strains belongs to or belong to one or more genera selected from the group comprising or, alternatively, consisting of: *Lactobacillus, Bifidobacterium, Streptococcus, Lactococcus, Akkermansia, Intestinimonas, Eubacterium, Faecalibacterium, Neisseria, Roseburia, Cutibacterium* and mixtures thereof. Said at least one strain or mixture of bacterial cell strains belongs to or belong to one or more species selected from the group comprising or, alternatively, consisting of: *Lactobacillus acidophilus, Lactobacillus buchneri, Lactobacillus fermentum, Lactobacillus salivarius* subsp. *salivarius, Lactobacillus crispatus, Lactobacillus paracasei* subsp. *paracasei, Lactobacillus gasseri, Lactobacillus plantarum, Lactobacillus delbrueckii* subsp. *bulgaricus, Lactobacillus delbrueckii* subsp. *delbrueckii, Lactobacillus rhamnosus, Lactobacillus pentosus, Lactobacillus fermentum, Lactobacillus brevis, Lactobacillus casei, Lactobacillus reuteri, Lactobacillus johnsonii, Bifidobacterium adolescentis, Bifidobacterium animalis* subsp, *lactis, Bifidobacterium breve, Bifobacterium catenulatum, Bifobacteriurn pseudocatenulatum, Bifidobacterium bifidum, Bifidobacterium lactis, Bifidobacterium infantis, Bifidobacterium longum, Akkermansia munichipila, Intestinimonas butyriciproducens, Eubacterium hallii, Faecalobacterium prausnitzii, Neisseria lactamica, Roseburia hominis, Cutibacterium acnes*, and mixtures thereof.

The crystalline gastroprotected granular bacteria of the invention may comprise or, alternatively, consist of a single bacterial strain or a mixture of bacterial strains belonging to the same species or to different species and/or genera as described in the present invention; in particular, it can be a mixture of 2, 3, 4, 5 or 6 different bacterial strains.

The crystalline gastroprotected granular bacteria of the invention may comprise a low % of bacteria not coated with said coating matrix.

The crystalline gastroprotected granular bacteria of the invention are preferably in solid form, in particular in the form of granules, powders, dried powders or freeze-dried powders.

Forming an object of the present invention is a composition (in short, composition of the invention) comprising a mixture comprising or, alternatively, consisting of granular bacteria gastroprotected with a coating matrix with crystalline structure according to any one of the embodiments of the invention and, optionally, said composition comprising at least one food grade or pharmaceutical or cosmetic additive and/or excipient.

The composition of the invention may be a pharmaceutical composition (Live Biotherapeutic Products, LBP) or a medical device composition or a cosmetic use composition, a dietary supplement or a food product (probiotic product) or a foods for special medical purposes (FSMP) or novel food.

Advantageously, the composition of the invention comprises said bacteria of the invention at a concentration comprised in the range from $1\times10^6$ AFU/g to $1\times10^{14}$ AFU/g, preferably from $1\times10^7$ AFU/g to $1\times10^{13}$ AFU/g, more preferably from $1\times10^8$ AFU/g to $1\times10^{12}$ AFU/g, wherein AFU/g (AFU; active fluorescent units) is measured using the flow cytometry method as defined in the present invention and it refers to bacteria with integral cell membrane on one gram of composition.

The composition of the invention optionally comprises said at least one pharmaceutical or food or cosmetic grade additive and/or excipient, i.e. a substance devoid of therapeutic activity suitable for pharmaceutical or food or cosmetic use. In the context of the present invention, the additives and/or excipients acceptable for pharmaceutical or food or cosmetic use comprise all the auxiliary substances known to the man skilled in the art for the preparation of compositions in solid, semi-solid or liquid form, such as, for example, diluents, solvents (including water, glycerine, ethyl alcohol), solubilizers, acidifiers, thickeners, sweeteners, flavour enhancers, colourants, lubricants, surfactants, preservatives, pH stabilizing buffers and mixtures thereof.

The composition of the invention, comprising the crystalline gastroprotected granular bacteria of the invention in the various embodiments described in the present invention, may be a pharmaceutical composition, or a medical device composition, or a composition for cosmetic use, or a dietary supplement composition or a food product composition or a food for special medical purposes (FSMP), all of these compositions referred to, for the sake of brevity, as the "compositions of the invention".

In the context of the present invention, the expression "medical device" is used in the meaning according to the Italian Legislative Decree no 46 dated 24 Feb. 1997 or according to the new Medical Device Regulation (EU) 2017/745 (MDR).

The composition of the invention may be in solid form, such as chewable solid, granules, flakes or powder, in semi-solid form, such as soft-gel, or in liquid form, such as solution, aqueous or hydroalcoholic or oily suspension, dispersion, emulsion or syrup.

For example, the composition of the invention may be a suspension of said granular bacteria gastroprotected with a coating matrix in crystalline form according to the invention in an oily phase, preferably vegetable oil.

Preferably, the composition of the invention is formulated for oral use.

Forming an object of the present invention is a process for the preparation of a granular bacteria gastroprotected with a coating matrix with a crystalline structure according to any one of the embodiments of the invention (in short, the process of the invention), comprising the steps of:

(I) granulating at least one strain or a mixture of bacterial cell strains (viable bacteria as such or bare or not coated), preferably bacteria in freeze-dried form, belonging to the bacterial species defined in the present description with meshes comprised in a range from 50 μm to 900 μm to obtain granular bacteria;

(II) coating said granular bacteria with a coating matrix comprising at least one lipid, preferably of plant origin, wherein said at least one lipid is selected from lipids of group A, preferably lipids of group B, more preferably the lipid of group B1 or the lipids of group B1 in association with the lipids of group B2 according to the examples reported in the present invention, to obtain gastroprotected granular bacteria as such; and (III) tempering (or maturation) said gastroprotected granular bacteria as such at a temperature comprised in the range from 2° C. to 60° C. for a period of time comprised in the range from 48 hours to 96 hours to obtain granular bacteria gastroprotected with a coating matrix with crystalline structure, wherein said at least one lipid preferably takes a lamellar configuration with crystalline structure following said tempering step (III), more preferably a multilayer crystalline structure-like lamellar configuration.

In an embodiment, the process of the invention comprising steps (I)-(III) further comprises, subsequently to step (III), step (IV) of carrying out bacterial count with an analytical method, preferably flow cytometry method as described hereinafter, on a sample of granular bacteria gastroprotected with a coating matrix with crystalline structure obtained from step (III), that allows to detect the amount of bacterial cells with integral (and therefore viable) cell membrane.

Preferably, in the process of the invention comprising steps (I) to (III) and, optionally step (VI), in step (I) the bacteria are granulated with meshes comprised in a range from 100 μm to 600 μm, preferably from 150 μm to 500 μm, more preferably from 180 μm or from 450 μm.

Preferably, in the process of the invention comprising steps (I) to (III) and, optionally step (VI), in step (II) said granular bacteria and said coating matrix are processed at a by weight ratio comprised in a range from 6:4 to 9:1, preferably from 6.5:3.5 to 8.5:1.5, more preferably from 7:3 to 8:2.

Preferably, in the process of the invention comprising steps (I) to (III) and, optionally step (VI), in step (III) said gastroprotected granular bacteria as such are tempered at a temperature comprised in the range from 30° C. to 40° C., preferably at about 35±1° C.

In an embodiment of the process of the invention, in step (I) said bacteria are granulated with meshes comprised in a range from 100 μm to 600 μm, preferably from 150 μm to 500 μm, more preferably from 180 μm or from 450 μm; in step (ii) said granular bacteria and said coating matrix, preferably wherein said coating matrix comprising at least one lipid of group A, preferably at least one lipid of group B, more preferably at least one lipid of group B1 or at least one lipid of group B1 in association with at least one lipid of group B2 according to the examples reported in the present invention, are processed at a by weight ratio comprised in a range from 6:4 to 9:1, preferably from 6.5:3.5 to 8.5:1.5, more preferably from 7:3 to 8:2; in step (III) said microencapsulated bacteria are tempered at a temperature at a temperature comprised in the range from 30° C. to 40° C., preferably of about 35±1° C., for a period of time comprised in the range from 60 hours to 84 hours, preferably about 72 hours; and, optionally, in step (IV) the bacterial count is carried out using flow cytofluorometric method.

In a preferred embodiment of the process of the invention, in step (I) said bacteria are granulated with 180 μm or 450 μm meshes; in step (II) said granular bacteria and said coating matrix, preferably wherein said coating matrix comprising at least one lipid of group A, preferably at least one lipid of group B, more preferably at least one lipid of group B1 or at least one lipid of group B1 in association with at least one lipid of group B2 according to the examples reported in the present invention, are processed at a by weight ratio from 7:3 to 8:2; in step (III) said microencapsulated bacteria are tempered at a temperature of about 35±1° C., for a period of time of about 72 hours; and, optionally, in step (IV) the bacterial count is carried out using the flow cytofluorometric method.

Said step (II) of coating said granular bacteria with a coating matrix comprising at least one lipid, preferably of plant origin, wherein said at least one lipid is selected from lipids of group A, preferably lipids of group B, more preferably the lipid of group B1 or the lipids of group B1 in association with the lipids of group B2 according to the examples reported in the present invention, to obtain gastroprotected granular bacteria as such, may be carried out according to techniques known to the man skilled in the art, such as for example spray techniques (spray of the coating matrix on granular bacteria).

In a preferred embodiment of the process of the invention, in step (II) said granular bacteria are coated with the coating matrix at a temperature comprised in the range from 40° C. to 60° C., more preferably to 50° C., in a fluid bed chamber (top-pray or bottom spray) with a bacteria: coating matrix ratio comprised in the range from 6.5:3.5 to 8.5:1.5, more preferably from 7:3 to 8:2; wherein the coating matrix comprises or, alternatively, consists of at least one lipid of group A, preferably at least one lipid of group B, more preferably at least one lipid of group B1 or at least one lipid of group B1 in association with at least one lipid of group B2 according to the examples reported in the present invention, as defined in the present invention.

In a preferred embodiment of the process of the invention, in step (III) said gastroprotected granular bacteria as such are tempered according to procedures known to the man skilled in the art.

Following a step for tempering the granulated bacteria coated with lipid matrix, also referred to as maturation of fat, the lipids take a spatial configuration that corresponds to a molecular structure in lamellae (lipid lamellae), with the lipid chains more or less perpendicular to the plane of the lamellae, as shown in FIG. 6. When the lipids take said spatial configuration, they are defined as "lamellar phase" lipids. In the leaves there can be a fluid (with no regular structure) or crystalline (packing type structure) structure, as shown in FIG. 7. Furthermore, the lipid lamellae can take a stacking structure of the lamellae forming lipid multilayers.

The process of the present invention, comprising said step (III) of tempering (or maturation of fat), results in the configuration of the lipid coating matrix in lamellae with crystalline structure wherein said lamellae are preferably stacked to form a crystalline lipid multilayer, and, thus, the preparation of granular bacteria gastroprotected with lipid coating matrix in crystalline form of the invention.

The flow cytometry analytical method preferably used in step (IV) of the process of the invention to detect the amount of bacterial cells with integral (viable) cell membranes is the analytical method described in patent application IT 102019000006056 on pages 33 line 24 to 35 line 17. In short, said flow cytometry analytical method comprises the steps of:

(VI.I) contacting a sample of gastroprotected granular bacteria with a coating matrix with a crystalline structure (in short, sample of bacteria of the invention) obtained from step (III) or a sample of the composition of the invention comprising the bacteria of the invention obtained from step (III) (in short, sample of the composition of the invention) with two different fluorescent dyes, so as to obtain a fluorescent sample of gastroprotected bacteria or composition of the invention; followed by (VI.II) by means of flow cytometry, detecting an amount of integral (and therefore viable) cell membranes in the fluorescent sample of gastroprotected bacteria or composition of the invention.

In particular, in the flow cytometry method, according to the method established by the ISO 19344:2015(E) standard, a first permeable dye through the cell membranes (preferably: thiazole orange or, alternatively, SYTO® 24—a fluorescent dye in the green spectrum) is capable of penetrating into all bacterial cells, by providing total fluorescent units or cells (TFU) of the fluorescent sample of gastroprotected bacteria or composition of the invention. A second dye (preferably: propidium iodide) is capable of penetrating only into the bacterial cells with a damaged cell membrane, providing the non-active or non-viable fluorescent units or cells (nAFU) of the fluorescent sample of gastroprotected bacteria or composition of the invention. Thus, the amount of viable bacterial cells, with integral cell membranes, may be expressed as active fluorescent units or cells (AFU), i.e. units that are only positive to the first dye in fluorescence analysis (preferably: thiazole orange or, alternatively, SYTO® 24), for which the following correlation applies: TFU=AFU+nAFU, where TFUs are the total fluorescent bacterial units or cells;

nAFUs are the non-active fluorescent bacterial units or cells, with a non-integral or damaged cell membrane (i.e. the units which are positive to the second dye, preferably propidium iodide).

According to an embodiment, the flow cytometer is configured and/or calibrated to perform a volumetric determination of the samples analysed comprising the bacteria of the invention, and to directly calculate the cell concentration (AFU and TFU).

Advantageously, to obtain the AFU and TFU values in the fluorescent sample of gastroprotected bacteria or composition of the invention, the flow cytofluorometer uses at least one internal fluorescent standard added to the fluorescent sample of gastroprotected bacteria or composition of the invention. In a preferred embodiment, the internal fluorescent standard is in the form of a fluorescent sphere or bead and it is added at known concentrations to each sample of bacteria of the invention or composition of the invention to be analysed. Thew value of AFU e di TFU of the fluorescent sample of gastroprotected bacteria or composition of the invention analysed may thus be calculated in proportion with respect to the known standard amounts.

Forming an object of the present invention is the crystalline gastroprotected granular bacteria of the present invention or the composition of the present invention for use as medicament in subjects in need.

The present invention relates to a method for the preventive or curative or medical treatment comprising administering an effective amount of crystalline gastroprotected granular bacteria of the present invention or the composition of the present invention to a subject in need.

Forming an object of the present invention is a cosmetic use of the bacteria of the present invention or of the composition of the present invention.

In the context of the present invention, the expression "subjects" is used to indicate human subjects or animal subjects (e.g. pets, such as dogs or cats or other mammals). Preferably, the compositions of the invention are for use in treatment methods for human subjects.

Unless otherwise specified, the expression composition comprises a component at an amount "comprised in a range from x to y" is used to indicate that said component can be present in the composition at all the amounts present in said range, even though not specified, extremes of the range comprised.

Unless otherwise specified, the expression gastroprotected crystalline granular bacterium of the invention or composition of the invention comprises a component at a %, said % being % by weight with respect to the total weight of the gastroprotected crystalline granular bacterium or composition.

Furthermore, the following embodiments (FRan) are object of the present invention.

FRa1. Granular bacteria gastroprotected with a coating matrix with crystalline structure, wherein said coating matrix comprises or, alternatively, consists of at least one lipid, wherein said at least one lipid has a lamellar configuration with crystalline structure, preferably a multilayer crystalline structure-like lamellar configuration.

FRa2. Bacteria according to FRa 1, wherein said at least one lipid is selected from the group comprising or, alternatively, consisting of:

mono-, di- or tri-glycerols esterified with saturated or unsaturated fatty acids, preferably saturated fatty acids;

free saturated fatty acids;

free unsaturated fatty acids, preferably mono-unsaturated;

mono-alcohols esterified with saturated or unsaturated fatty acids, preferably saturated fatty acids;

di-alcohols esterified with saturated or unsaturated fatty acids, preferably saturated fatty acids;

sucrose fatty acid esters (sucresters), preferably mixtures of mono- di- and/or tri-sucrose fatty acid esters;

wherein said saturated or unsaturated fatty acids, free or esterified with glycerol or mono-alcohols or di-alcohols or sucrose, have a number of carbon atoms comprised in the range from C6 to C32, preferably from C14 to C24, more preferably C16, C18 and/or C22.

FRa 3. Bacteria according to FRa 2, wherein said at least one lipid, preferably of plant origin, comprises:

at least one first lipid, wherein said first lipid is a mono-, di- or tri-glycerols esterified with saturated or unsaturated fatty acids, preferably saturated fatty acids; and at least one second lipid, wherein said second lipid is a sucrose fatty acid ester (sucrester), preferably a mixture of mono- di- and/or tri-sucrose fatty acid esters;

wherein said fatty acids esterified with the glycerol or with the sucrose have a number of carbon atoms comprised in the range from C6 to C32, preferably from C14 to C24, more preferably C16, C18, C20 and/or C22.

FRa 4. Bacteria according to any one of claims 1 to 3, wherein the bacteria as such are comprised in a by weight % comprised in the range from 60% to 90%, and the coating matrix comprising, or alternatively, consisting of at least one lipid is comprised in a by weight % comprised in the range from 10% to 40%, with respect to the total weight of gastroprotected granular bacteria; preferably the bacteria as such from 65% to 85% and the coating matrix from 15% to 35%; more preferably the bacteria as such from 70% to 80% and the coating matrix from 20% to 30%.

FRa 5. A composition comprising a mixture comprising, or alternatively, consisting of said bacteria according to any one of FRas 1 to 4 and, optionally, said composition comprises at least one food grade or pharmaceutical or cosmetic additive and/or excipient.

FRa 6. The composition according to FRa 5, wherein said bacteria according to any one of claims 1 to 5 are comprised in a concentration comprised in the range from $1\times10^6$ AFU/g to $1\times10^{14}$ AFU/g, preferably from $1\times10^7$ AFU/g to $1\times10^{13}$ AFU/g, more preferably from $1\times10^8$ AFU/g to $1\times10^{12}$ AFU/g, wherein AFU/g refers to viable cells and with integral cell membrane on one gram of composition.

FRa 7. A process for the preparation of bacteria according to any one of FRas 1 to 4 comprising the steps of:

(I) granulating at least one bacterial cell strain with meshes comprised in a range from 50 microns to 900 microns to obtain granular bacteria;

(II) coating said granular bacteria with a coating matrix comprising at least one lipid, preferably of plant origin, according to claim 3 or 4 to obtain gastroprotected granular bacteria as such; and (III) tempering said gastroprotected granular bacteria as such at a temperature comprised in the range from 25° C. to 60° C. for a period of time comprised in the range from 48 hours to 96 hours to obtain granular bacteria gastroprotected with a coating matrix with crystalline structure; preferably, wherein said at least one lipid takes a lamellar configuration with crystalline structure following said tempering step (III).

FRa 8. The method according to FRa 7, wherein said process further comprises, subsequently to said step (III), the step (IV) of performing the bacterial count using an analytical method on a sample of granular bacteria gastroprotected with a coating matrix with crystalline structure obtained from step (III), wherein said analytical method allows to detect the amount of bacterial cells with integral cell membrane; preferably, said analytical method is a flow cytometry.

FRa 9. The method according to FRa 7 or 8, wherein in step (I) said bacteria are granulated with links comprised in a range from 100 microns to 600 microns, preferably from 150 to 500 microns, more preferably from 180 microns or from 450 microns; wherein in step (II), preferably carried out in a fluid bed chamber, said granular bacteria and said coating matrix are processed at a by weight ratio comprised in a range from 6:4 to 9:1, preferably from 6.5:3.5 to 8.5:1.5, more preferably from 7:3 to 8:2; and wherein in step (III) said gastroprotected granular bacteria as such are tempered at a temperature comprised in the range from 30° C. to 40° C., preferably at about 35÷1° C., for a period of time comprised in the range from 60 hours to 84 hours, preferably about 72 hours.

FRa 10. Granular bacteria gastroprotected with a coating matrix with crystalline structure that can be obtained according to the process according to FRa 7-9.

Furthermore, the following embodiments (FRbn) are object of the present invention.

FRb1. Granular bacteria gastroprotected with a coating matrix with crystalline structure, wherein said coating matrix comprises or, alternatively, consists of at least one lipid, wherein said at least one lipid has a lamellar configuration with crystalline structure, preferably a multilayer crystalline structure-like lamellar configuration.

FRb 2. Bacteria according to FRb 1, wherein said at least one lipid is selected from the group comprising or, alternatively, consisting of:

mono-, di- or tri-glycerols esterified with saturated or unsaturated fatty acids, preferably saturated fatty acids;

free saturated fatty acids;

free unsaturated fatty acids, preferably mono-unsaturated;

mono-alcohols esterified with saturated or unsaturated fatty acids, preferably saturated fatty acids;

di-alcohols esterified with saturated or unsaturated fatty acids, preferably saturated fatty acids;

sucrose fatty acid esters (sucresters), preferably mixtures of mono- di- and/or tri-sucrose fatty acid esters;

wherein said saturated or unsaturated fatty acids, free or esterified with glycerol or mono-alcohols or di-alcohols or sucrose, have a number of carbon atoms comprised in the range from C6 to C32, preferably from C14 to C24, more preferably C16, C18 and/or C22.

FRb 3. Bacteria according to FRb 2, wherein said at least one lipid, preferably of plant origin, comprises:

at least one first lipid, wherein said first lipid is a mono-, di- or tri-glycerols esterified with saturated or unsaturated fatty acids, preferably saturated fatty acids; and at least one second lipid, wherein said second lipid is a sucrose fatty acid ester (sucrester), preferably a mixture of mono- di- and/or tri-sucrose fatty acid esters;

wherein said fatty acids esterified with the glycerol or with the sucrose have a number of carbon atoms comprised in the range from C6 to C32, preferably from C14 to C24, more preferably C16, C18, C20 and/or C22.

FRb 4. Bacteria according to any one of FRbs 1 to 3, wherein the bacteria as such are comprised in a by weight % comprised in the range from 60% to 90%, and the coating matrix comprising, or alternatively, consisting of at least one lipid is comprised in a by weight % comprised in the range from 10% to 40%, with respect to the total weight of gastroprotected granular bacteria; preferably the bacteria as such from 65% to 85% and the coating matrix from 15% to 35%; more preferably the bacteria as such from 70% to 80% and the coating matrix from 20% to 30%.

FRb 5. A composition comprising a mixture comprising, or alternatively, consisting of said bacteria according to any one of FRbs 1 to 4 and, optionally, said composition comprises at least one food grade or pharmaceutical or cosmetic additive and/or excipient.

FRb 6. The composition according to FRb 5, wherein said bacteria according to any one of claims 1 to 5 are comprised in a concentration comprised in the range from $1\times10^6$ AFU/g to $1\times10^{14}$ AFU/g, preferably from $1\times10^7$ AFU/g to $1\times10^{13}$ AFU/g, more preferably from $1\times10^8$ AFU/g to $1\times10^{12}$ AFU/g, wherein AFU/g refers to viable cells and with integral cell membrane on one gram of composition.

FRb 7. A process for the preparation of bacteria according to any one of FRbs 1 to 4 comprising the steps of:

(I) granulating at least one bacterial cell strain with meshes comprised in a range from 50 microns to 900 microns to obtain granular bacteria;

(II) coating said granular bacteria with a coating matrix comprising at least one lipid, preferably of plant origin, according to claim 3 or 4 to obtain gastroprotected granular bacteria as such; and (III) tempering said gastroprotected granular bacteria as such at a temperature comprised in the range from 25° C. to 60° C. for a period of time comprised in the range from 48 hours to 96 hours to obtain granular bacteria gastroprotected with a coating matrix with crystalline structure; preferably, wherein said at least one lipid takes a lamellar configuration with crystalline structure following said tempering step (III).

FRb 8. The method according to FRb 7, wherein said process further comprises, subsequently to said step (III), the step (IV) of performing the bacterial count using an analytical method on a sample of granular bacteria gastroprotected with a coating matrix with crystalline structure obtained from step (III), wherein said analytical method allows to detect the amount of bacterial cells with integral cell membrane; preferably, said analytical method is a flow cytometry.

FRb 9. The method according to FRb 7 or 8, wherein in step (I) said bacteria are granulated with links comprised in a range from 100 microns to 600 microns, preferably from 150 to 500 microns, more preferably from 180 microns or from 450 microns; wherein in step (II), preferably carried out in a fluid bed chamber, said granular bacteria and said coating matrix are processed at a by weight ratio comprised in a range from 6:4 to 9:1, preferably from 6.5:3.5 to 8.5:1.5, more preferably from 7:3 to 8:2; and wherein in step (III) said gastroprotected granular bacteria as such are tempered at a temperature comprised in the range from 30° C. to 40° C., preferably at about 35+1° C., for a period of time comprised in the range from 60 hours to 84 hours, preferably about 72 hours.

FRb 10. Granular bacteria gastroprotected with a coating matrix with crystalline structure that can be obtained according to the process according to FRb 7-9.

Experimental Part 1

The studies reported below (trial B and C) aim to view the morphology of the coatings of the samples under analysis and to compare them with their crystallographic structure. In addition, study A aims to analyse the viability of the bacterial strains comprised in the samples under analysis.

Materials and Method

Samples Analysed

Sample 0 (WBR05018): freeze-dried bacterial strain not granulated, not coated and not tempered.

Sample 1: GG 107-18 (450 μm, bare) strain granulated to 450 microns; NOT coated; NOT tempered.

Sample 2: GG107-18 (180 μm, bare) strain granulated to 180 microns; NOT coated; NOT tempered.

Sample 3: MCPM-P1 (450 μm, coated) strain granulated to 450 microns; coated with a coating matrix comprising the lipid (i) Biogapress Vegetal BM297 ATO manufactured by Gattefossé SAS E471 (in short, Biogapress Vegetal E471); coating method: at 50° C. fluid bed chamber with an 80% strain\20% Biogaress Vegetal E471 ratio; NOT tempered, stored at −20° C.

Sample 4: MCPM-P2 (180 μm, coated) strain granulated to 180 microns; coated with a coating matrix comprising the lipid (i) Biogapress Vegetal E471 at 50° C. fluid bed chamber with an 80% strain\20% Biogapress Vegetal E471 ratio; NON tempered, stored at −20° C.

Sample 5: MCPM-P1/20 (450 μm, coated+matured 35° C., 72 h) strain granulated to 450 microns; coated with a coating matrix comprising the lipid (i) Biogapress Vegetal E471 50° C. fluid bed chamber with an 80% strain\20% Biogapress Vegetal E471 ratio; tempered at 35° C. for 72 hrs, stored at −20° C.

Sample 6: MCPM-P2/20 (180 μm, coated+matured 35° C., 72 hrs) strain granulated to 180 microns; coated with a coating matrix comprising the lipid (i) Biogapress Vegetal E471 at 50° C. fluid bed chamber with an 80% strain\20% Biogapress Vegetal E471 ratio; tempered at 35° C. for 72 hrs, stored at −20° C.

Samples 0-6 are in powder form.

Bacterial strain used for Samples 0 and 1-6: *Lactobacillus rhamnosus* GG ATCC 53103.

The granulating dimensions are defined by the granulator mesh, in the examples 180 μm or 450 μm granules respectively were evaluated Analytical Methods (A) Flow Cytometry Analytical Method.

Flow cytometry analytical method used according to the method established by the ISO 19344:2015(E) standard. Said method was applied to Samples 1-6 at time $t_0$, i.e. after the preparation thereof and prior to the submission thereof to electron microscopy (SEM) and X-ray diffraction analysis (see paragraph (B) and (C)).

TFUs are total bacterial units or cells;

AFUs are bacterial units or cells with an integral (or viable) cell membrane.

Samples were stored at −20° C. (standard storage).

(B) X-Ray Diffraction Analysis (FIG. 1).

Analytical method used: X-ray diffraction to characterise the crystalline structure of lipids.

Said method was applied to samples 1, 4, 5 and 6.

Preparation of the sample: the sample in powder form was introduced into a 1 mm diameter glass capillary.

Diffraction:

Transmission setting

Beamline PROXIMA 2 al sincrotrone SOLEIL (France)

Wavelength: 0.7293 Å,

Distance of the sample detector: 400 mm

2D DECTRIS (pixel 75×75 $\mu m^2$) detector

T=22° C., HR 40%

Analysis: X-ray patterns were analysed using the ESIT FIT2D software and compared to each other.

The intensity profiles shown in this report correspond to angular profiles integrated at 180°.

The diffraction setting allows to collect the SAXS and WAXS diffraction patterns.

SAXS patterns provide information on the stacking structure of lipid lamellae (reticular distance, crystallite size) and WAXS patterns give lateral order information within the lipid layers.

(C) Electron Microscopy (SEM)

Analytical method used: SEM FEG (low voltage SEM) to observe the surface of the coatings in order to evaluate the quality of the coating.

Said method was applied to samples 1, 4, 5 and 6.

Preparation of the sample: the powders were deposited on a carbon adhesive fixed on the medium.

Care was taken not to crush the powder and not to overload the deposit.

Acquisition of the image: observations were made on SUPE 55VP di ZEISS electron microscope.

The 1.20 kV voltage was chosen to obtain the best compromise between intensity, surface charge and stability of the product under the electron beam.

Images with different magnifications (×200, ×500, ×1500, ×3000 and ×8000) were acquired to cover a wide field of view and see high-resolution details.

Results (A) Flow Cytometry Analytical Method

From the bacterial count in flow cytometry of Samples 1-6 it was observed that (Table 1):

- Samples 1-6 are homogeneous because the TFU data, which identifies the TOTAL cell count, remains constant for samples 1-3-5 (450 μm granulation) and 2-4-6 (180 μm granulation), which means that the observations made in the analyses (B) and (C) are consistent;
- the process mortality evaluated in AFU (viable/integral cell count) is not inferred, given starting from the bare bacterial strain at the two different grain sizes (Samples 1 and 2) the AFU data remains practically unchanged in the process of coating with lipid matrix (Samples 3 and 4) and tempering (Samples 5 and 6).

TABLE 1

| | Sample | | at $t_0$, after preparation |
|---|---|---|---|
| 1 | GG 107-18 (450 μm, bare) | AFU | 1.11E+12 |
| | | TFU | 1.47E+12 |
| 2 | GG 107-18 (180 μm, bare) | AFU | 1.07E+12 |
| | | TFU | 1.41E+12 |
| 3 | MCPM-P1 (450 μm, coated) | AFU | 1.16E+12 |
| | | TFU | 1.45E+12 |
| 4 | MCPM P2 (180 μm, coated) | AFU | 1.06E+12 |
| | | TFU | 1.38E+12 |
| 5 | MCPM-P1/20 (450 μm, coated + tempered*) | AFU | 1.09E+12 |
| | | TFU | 1.29E+12 |
| 6 | MCPM-P2/20 (180 μm, coated + tempered*) | AFU | 1.02E+12 |
| | | TFU | 1.21E+12 |

*35° C. for 72 hours (B) X-Ray Diffraction Analysis.

(C.I) Sample 1 (FIGS. 2-5).

Sample 1 (non-granular, uncoated freeze-dried bacterial cell) is totally amorphous (absence of sharp diffraction characteristics).

(C.ii) Samples 4, 5 and 6 (FIGS. 2-5).

Samples 4, 5 and 6 are characterised by a series of characteristic diffractions in the SAXS and WAXS regions.

It should be noted that the signals of the Samples 5 and 6 are almost the same both in position and in intensity.

WAXS Region (FIG. 4)

All samples 4, 5 and 6 show a peak at 4.1 Å (hexagonal packing of the lipid).

For samples 5 and 6, several WAXS peaks were also observed at around 4.1 Å, which means that other intra-lamellar reticula of a hexagonal reticulum coexist in the lipid layers.

SAXS Region (FIG. 5)

Samples 5 and 6 show an acute peak at 49.8 Å (and its harmonics), and Sample 4 at 52 Å (and its harmonics).

The position of these peaks is linked to the reticular distance of the stack of lipid lamellae.

The comparison of the crystalline characteristics of Samples 1, 4, 5 and 6 is shown in Table 2:

TABLE 2

| | Number of crystalline systems | |
|---|---|---|
| | Lateral | Lamellar (reticular distance) |
| Sample 1 | 0 (amorphous) | 0 (amorphous) |
| Sample 4 | 1 | 1 (52.0 Å) |
| Sample 5 | Co-existence of 2 or higher | 1 (49.8 Å) |
| Sample 6 | Co-existence of 2 or higher | 1 (49.8 Å) |

In conclusion:

- Sample 1 is purely amorphous, no trace of any lamellar order;
- all Samples 4, 5 and 6 show only one lamellar system. The reticular distance changes slightly from one sample to another;
- a system with hexagonal lateral order is present in all Samples 4, 5 and 6;
- a second lateral system is also detectable in samples 5 and 6;
- Samples 5 and 6 have the same crystallographic structure.

Except for Sample 1 which is totally amorphous (absence of sharp diffraction characteristics), all other samples are characterised by typical lipid diffraction patterns with "lamellar phase".

"Lamellar phase" is a spatial configuration of the lipids corresponding to the molecular structure in lamellae, with the lipid chains more or less perpendicular to the plane of the lamellae, as shown in FIG. 6.

In summary:

- Sample 1: WAXS and SAXS data show the absence of a coating;
- Sample 4: WAXS and SAXS data confirm the existence of a non-multilayer coating;
- Samples 5 and 6: WAXS and SAXS data confirm the existence of a multilayer coating.

(C) Electron Microscopy (SEM)

Sample 1

Sample 1 shows large, irregular-shaped structures with typical dimensions of several hundred micrometres (FIG. 8). These structures are linked and form larger three-dimensional objects (up to millimetres). The low magnification surface has reliefs and roughness but is overall smooth.

At a larger magnification (FIG. 9), the surface of Sample 1 shows stripes or geometric patterns and sometimes it appears more granular. It can be noted that bacillary bacteria (size of the order of 0.5×2 microns) can be frequently observed by forming a very narrow carpet.

The form of the Bacteria, conferred by the cell wall, may be due to three basic types: coccacea or spheroidal, bacillary: The bacillary form has a longer cell axis than the others.

Sample 4 (MCPM-P2)

Sample 4 shows a mixture of small grains, larger particles with irregular shape and flat particles (FIG. 10). In high magnification sample 4, no bacteria were clearly observed (FIG. 11).

Sample 5 (MCPM-P1/20)

Sample 5 shows a mixture of large flat particles (a few tens or hundreds of μm) and small spherical or irregular shaped particles (from a few μm to a few tens of μm). Their surfaces are slightly rough and show roughness (FIG. 12). At high magnification (FIG. 13), the bacteria are slightly visible locally. The surfaces are quite smooth with some roughness and particles.

Sample 6 (MCPM-P2/20)

Sample 6 shows a mixture of small grains, larger particles with irregular shape and flat particles (FIG. 14). At high magnification (FIG. 15), the surfaces are quite smooth, but some particles are visible and the bacteria are slightly visible.

The comparison of the characteristics of Samples 1, 4, 5 and 6 under an electron microscope is shown in table 3:

TABLE 3

| | Powder appearance | Surface appearance | Observation of the bacteria (intended as presence of bare, uncoated bacteria) |
|---|---|---|---|
| Sample 1 | Molten | smooth | yes |
| Sample 4 | Granular and aggregated | Smooth with particles | No |
| Sample 5 | Granular and aggregated | Smooth with particles and roughness | mild |
| Sample 6 | Granular and aggregated | Smooth with particles | mild |

Table 3 is correct, the data are as obtained from the two reports and thus do not have to be done over again.

In summary:

Samples 1 and 2: the bacterial strain is clearly visible under an electron microscope;

Samples 3, 4, 5 and 6: disappearance\reduction of microorganisms in optical fields. No bare samples are observed in these samples, this is an indication of an effective microencapsulation.

Discussion of the Results

1) The non-granulated freeze-dried bacterial strains (comparative blank) are clearly distinguishable by means of electron microscopy (SEM); furthermore, the X-ray diffraction analysis does not show any coating.

2) The freeze-dried bare strains were granulated with two different meshes at 180 μm and 450 μm, coated with Biogapress Vegetal E471 and, optionally, tempered to obtain Sample 4 (not tempered) or Samples 5 and 6 (tempered).

Electron microscopy (SEM) shows that bacterial strains are coated both in Sample 4 and in Samples 5 and 6.

The X-ray diffraction analysis (WAXS and SAXS) shows—in Samples 5 and 6—the presence of a crystalline multilayer which is not present in Sample 4 since the tempering step was not carried out considering the same process.

Finally, by means of flow cytometry analysis, the absence of process mortality was observed for the bacterial strains of samples 5 and 6 subjected to the granulation, coating and tempering steps according to the invention.

Therefore, by means of the process according to the invention it is possible to coat the granular bacterial strains effectively with a lipid matrix and, by means of a tempering process, to obtain a good crystallisation (development of a lateral multilayer) while maintaining the concentration of viable bacterial strains unchanged or almost unchanged before and after the granulation, coating and tempering process of the invention.

Experimental Part 2

The study reported below (study D) compares the bacterial viability (bacterial load) of a bare bacterial strain and its corresponding gastroprotected one with a coating matrix in crystalline form according to the invention after being subjected to heating at controlled humidity.

Materials and Method of Trial D

Samples Analysed

Sample 7: Bare bacterial strain *Lactobacillus rhamnosus* GG ATCC 53103 (uncoated and not tempered); in short, bare uncoated bacterial strain.

Sample 8: Bacterial strain *Lactobacillus rhamnosus* GG ATCC 53103 gastroprotected with coating matrix in crystalline form according to the present invention (coated and tempered): the coating matrix comprises the lipid (i) Biogaress Vegetal E471; for example: coating 50° C. fluid bed chamber with an 80% strain\20% Biogaress Vegetal E471 ratio; tempering at 35° C. for 72 hrs; in short, coated bacterial strain.

Methodology

Trial D was conducted by dosing samples 7 and 8 (bare and coated bacterial strain) in vegetable oil to form bacterial suspensions in oil. Said bacterial suspensions in vegetable oil were subjected to two different temperatures and controlled humidity (RH: Relative humidity), such as: 30° C. —75% RH (FIG. 16) and 40° C. —75% RH (FIG. 17), respectively for a time range of 0 to 12 months and 0 to 60 days. During said time range, the viability of the bacterial strains of the two samples (samples 7 and 8) was measured.

Analytical Method

The viability of the bacterial strains (bacterial load) was evaluated by means of cytometry method (data expressed in AFU).

Flow cytometry analytical method used according to the method established by the ISO 19344:2015(E) standard.

AFUs are bacterial units or cells with an integral (or viable) cell membrane.

Results

As reported in FIGS. 16 and 17, the load of the coated bacterial strain is a greater logarithm with respect to the bare bacterial strain, both at 60 days at 40° C. and at 12 months at 30° C. Thus, it is clear that the gastroprotected bacterial strain with a coating matrix in crystalline form according to the present invention is more resistant than the bare bacterial strain considering the same temperature and humidity.

The invention claimed is:

1. Bacterial granules gastroprotected with a lipid coating matrix with crystalline structure, wherein said coating matrix comprises at least one lipid comprising saturated fatty acids having a number of carbon atoms in the range from C14 to C24 said at least one lipid being in a multilayer crystalline lamellar configuration forming a crystalline laminar structure of the lipid coating matrix.

2. The bacterial granules according to claim 1, wherein said coating matrix further comprises at least one additional lipid selected from:

mono-, di- or tri-glycerols esterified with saturated or unsaturated fatty acids, preferably saturated fatty acids;

free saturated fatty acids;

free unsaturated fatty acids;

mono-alcohols esterified with saturated or unsaturated fatty acids;

di-alcohols esterified with saturated or unsaturated fatty acids; and sucrose fatty acid esters (sucresters);

wherein said saturated or unsaturated fatty acids, free or esterified with glycerol or mono-alcohols or di-alcohols or sucrose, have a number of carbon atoms comprised in a range from C6 to C32.

3. The bacterial granules according to claim 2, wherein said at least one additional lipid, comprises:

at least one first lipid, wherein said first lipid is a mono-, di- or tri-glycerols esterified with saturated or unsaturated fatty acids; and at least one second lipid, wherein said second lipid is a sucrose fatty acid ester (sucrester);

wherein said fatty acids esterified with the glycerol or with the sucrose have a number of carbon atoms comprised in a range from C6 to C32.

4. The bacterial granules according to claim 2, wherein the mono-alcohols are esterified with saturated fatty acids.

5. The bacterial granules according to claim 2, wherein the sucrose fatty acid esters (sucresters) comprise mixtures of mono-, di- and/or tri-sucrose fatty acid esters.

6. The bacterial granules according to claim 2, wherein said saturated or unsaturated fatty acids, free or esterified with glycerol or mono-alcohols or di-alcohols or sucrose, have a number of carbon atoms comprised in the range from C14 to C24, C16, C18 and/or C22.

7. The bacterial granules according to claim 1, wherein bacteria are comprised by weight % ranging from 60% to 90%, and the coating matrix comprising at least one lipid by weight % comprised in a range from 10% to 40%, with respect to the total weight of gastroprotected bacterial granules.

8. The bacterial granules according to claim 1, wherein the bacteria are comprised by weight % ranging from 65% to 85%, and the coating matrix comprising at least one lipid by weight % ranging from 15% to 35%, with respect to the total weight of gastroprotected bacterial granules.

9. The bacterial granules according to claim 1, wherein the bacteria are comprised by weight % ranging from 70% to 80%, and the coating matrix comprising at least one lipid by weight % ranging from 20% to 30%, with respect to the total weight of gastroprotected bacterial granules.

10. The bacterial granules according to claim 1, wherein said saturated fatty acids have a number of carbon atoms in a range selected from C16 to C18, and C16 to C22.

11. The bacterial granules according to claim 1, wherein said saturated fatty acids have a number of carbon atoms selected from the group consisting of C16, C18, C20, and C22.

12. The bacterial granules according to claim 1, wherein said at least one lipid comprises a mixture of mono- and di-glycerides esterified with said saturated fatty acids.

13. The bacterial granules according to claim 1, wherein said at least one lipid is selected from the group consisting of glyceryl dipalmitostearate, glyceryl palmitostearate, glyceryl dibehenate, and mixtures thereof.

14. The bacterial granules according to claim 1, wherein the multilayer crystalline lamellar configuration comprises a hexagonal lateral order characterized by a peak at 4.1 Å, as determined by Wide Angle X-ray Scattering (WAXS).

15. The bacterial granules according to claim 1, wherein the multilayer crystalline lamellar configuration comprises a lamellar system having a reticular distance of 49.8 Å, as determined by Small Angle X-ray Scattering (SAXS).

16. The bacterial granules according to claim 1, wherein the crystalline laminar structure of the lipid coating matrix is obtained by a tempering process at a temperature in the range from 25° C. to 60° C. for a period of time in the range from 48 hours to 96 hours.

17. The bacterial granules according to claim 16, wherein the tempering process is performed at a temperature in the range from 30° C. to 40° C. for a period of time in the range from 60 hours to 84 hours.

18. The bacterial granules according to claim 1, wherein the bacteria comprise at least one bacterial strain belonging to a genus selected from the group consisting of *Lactobacillus* and *Bifidobacterium.*

19. The bacterial granules according to claim 18, wherein the at least one bacterial strain comprises *Lactobacillus rhamnosus.*

20. The bacterial granules according to claim 1, wherein the bacteria are in a freeze-dried form within the lipid coating matrix.

21. The bacterial granules according to claim 1, wherein the bacterial granules have a size corresponding to granulation with meshes in a range from 100 μm to 600 μm.

22. The bacterial granules according to claim 21, wherein the bacterial granules have a size corresponding to granulation with meshes in a range from 150 μm to 500 μm.

23. The bacterial granules according to claim 1, wherein the bacteria comprise a mixture of 2, 3, 4, 5, or 6 different bacterial strains.

24. A composition comprising a mixture of the bacterial granules according to claim 1 in which the bacteria comprise strains belonging to a same or different species and/or genera and, optionally at least one food grade or pharmaceutical or cosmetic additive and/or excipient.

25. The composition according to claim 24, wherein bacterial granules are in a concentration comprised in a range from $1\times10^6$ AFU/g to $1\times10^{14}$ AFU/g, wherein AFU/g refers to viable cells and with integral cell membranes on one gram of composition.

26. The composition according to claim 24, wherein said bacteria are comprised in a concentration comprised in the range from $1\times10^7$ AFU/g to $1\times10^{13}$ AFU/g, wherein AFU/g refers to viable cells and with integral cell membranes on one gram of composition.

27. The composition according to claim 24, wherein said bacteria are comprised in a concentration comprised in the range from $1\times10^8$ AFU/g to $1\times10^{12}$ AFU/g, wherein AFU/g refers to viable cells and with integral cell membranes on one gram of composition.

28. A composition comprising a mixture of the bacterial granules according to claim 1 and at least one food grade or pharmaceutical or cosmetic additive and/or excipient.

29. A process for the preparation of bacteria according to claim 1, the process comprising the steps of:

granulating at least one bacterial cell strain with meshes comprised in a range from 50 microns to 900 microns to obtain bacterial granules;

coating said bacterial granules with a coating matrix comprising the at least one lipid to obtain gastroprotected bacterial granules as such; and tempering said gastroprotected bacterial granules as such at a temperature in the range from 25° C. to 60° C. for a period of time in the range from 48 hours to 96 hours to obtain bacterial granules gastroprotected with a coating matrix with crystalline structure.

30. The process according to claim 29, wherein said process further comprises, subsequently to the tempering, the step of performing the bacterial count using an analytical method on a sample of bacterial granules gastroprotected with a coating matrix with crystalline structure obtained from the tempering wherein said analytical method allows to detect the amount of bacterial cells with integral cell membrane.

31. The process according to claim 29, wherein the granulating is performed by granulating said bacteria with meshes in a range from 100 microns to 600 microns;

wherein the coating is performed by processing said bacterial granules and said coating matrix at a by weight ratio in a range from 6:4 to 9:1; and wherein the tempering is performed by tempering said gastroprotected bacterial granules at a temperature in the range from 30° C. to 40° C., for a period of time in the range from 60 hours to 84 hours.

32. Bacterial granules gastroprotected with a coating matrix with crystalline structure obtained according to the process comprising the steps of:

granulating at least one bacterial cell strain with meshes comprised in a range from 50 microns to 900 microns to obtain bacterial granules;

coating said bacterial granules with a coating matrix comprising the at least one lipid to obtain gastroprotected bacterial granules as such; and tempering said gastroprotected bacterial granules as such at a temperature in the range from 25° C. to 60° C. for a period of time in the range from 48 hours to 96 hours to obtain bacterial granules gastroprotected with a coating matrix with crystalline structure.

33. Bacterial granules gastroprotected with a coating matrix with crystalline structure, wherein said coating matrix consists of at least one lipid selected from mono-, di- and tri-glycerides esterified with saturated fatty acids having a number of carbon atoms in the range from C14 to C24, wherein said at least one lipid has a multilayer crystalline lamellar configuration forming a crystalline laminar structure of the coating matrix.

* * * * *